United States Patent
Scheller et al.

(10) Patent No.: US 9,877,867 B2
(45) Date of Patent: *Jan. 30, 2018

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 467 days.

This patent is subject to a terminal disclaimer.

(21) Appl. No.: 13/939,250

(22) Filed: Jul. 11, 2013

(65) Prior Publication Data
US 2014/0039471 A1    Feb. 6, 2014

Related U.S. Application Data

(60) Provisional application No. 61/678,591, filed on Aug. 1, 2012.

(51) Int. Cl.
*A61B 18/18* (2006.01)
*A61F 9/008* (2006.01)
*A61B 18/22* (2006.01)

(52) U.S. Cl.
CPC .. *A61F 9/00823* (2013.01); *A61B 2018/2238* (2013.01); *A61F 2009/00863* (2013.01)

(58) Field of Classification Search
CPC ...... A61F 9/008; A61F 9/00821; A61B 18/20; A61B 18/22
USPC ................................. 606/4, 11, 16
See application file for complete search history.

(56) References Cited

U.S. PATENT DOCUMENTS

| | | | | |
|---|---|---|---|---|
| 4,687,293 A | * | 8/1987 | Randazzo | G02B 6/4402 385/102 |
| 5,190,050 A | | 3/1993 | Nitzsche | |
| 5,228,852 A | * | 7/1993 | Goldsmith | A61C 1/0046 433/141 |

(Continued)

FOREIGN PATENT DOCUMENTS

| | | |
|---|---|---|
| EP | 0900547 B1 | 3/1999 |
| WO | WO 2006/091597 A1 | 8/2006 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — William Thomson
*Assistant Examiner* — Sebastian X Lukjan
(74) *Attorney, Agent, or Firm* — Kevin P. Rollins

(57) ABSTRACT

A steerable laser probe may include a handle having a handle distal end and a handle proximal end, a plurality of actuation controls of the handle, a housing tube having a housing tube distal end and a housing tube proximal end, and an optic fiber disposed within an inner bore of the handle and the housing tube. An actuation of an actuation control of the plurality of actuation controls may gradually curve the housing tube. A gradual curving of the housing tube may gradually curve the optic fiber. An actuation of an actuation control of the plurality of actuation controls may gradually straighten the housing tube. A gradual straightening of the housing tube may gradually straighten the optic fiber.

20 Claims, 29 Drawing Sheets

(56) References Cited

U.S. PATENT DOCUMENTS

| | | |
|---|---|---|
| 5,355,871 A | 10/1994 | Hurley et al. |
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 5,951,544 A * | 9/1999 | Konwitz ............... A61B 18/22 606/13 |
| 6,123,699 A | 9/2000 | Webster, Jr. |
| 6,126,654 A | 10/2000 | Giba et al. |
| 6,198,974 B1 * | 3/2001 | Webster, Jr. ...... A61M 25/0136 600/146 |
| 6,488,695 B1 | 12/2002 | Hickingbotham |
| 6,505,530 B2 | 1/2003 | Adler et al. |
| 6,530,913 B1 | 3/2003 | Giba et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 * | 12/2009 | Griffin ............ A61B 17/22032 604/102.01 |
| 7,766,904 B2 | 10/2010 | McGowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0065504 A1 * | 3/2005 | Melsky ................ A61B 18/22 606/16 |
| 2005/0157985 A1 | 7/2005 | McGowan, Sr. et al. |
| 2005/0272975 A1 | 12/2005 | McWeeny et al. |
| 2007/0185514 A1 | 8/2007 | Kirchhevel |
| 2007/0260231 A1 * | 11/2007 | Rose ..................... A61B 18/22 606/13 |
| 2009/0018993 A1 | 1/2009 | Dick et al. |
| 2009/0187170 A1 | 7/2009 | Auld et al. |
| 2009/0312750 A1 | 12/2009 | Spaide |
| 2010/0004642 A1 * | 1/2010 | Lumpkin ............... A61B 18/22 606/4 |
| 2010/0268234 A1 | 10/2010 | Aho et al. |
| 2011/0028947 A1 | 2/2011 | Scheller et al. |
| 2012/0116361 A1 | 5/2012 | Hanlon et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |

\* cited by examiner

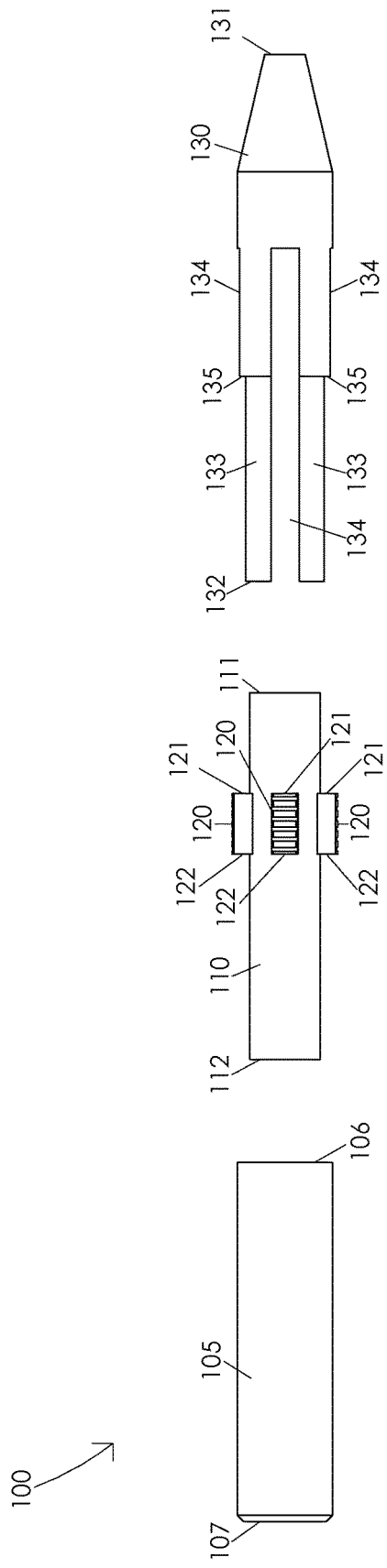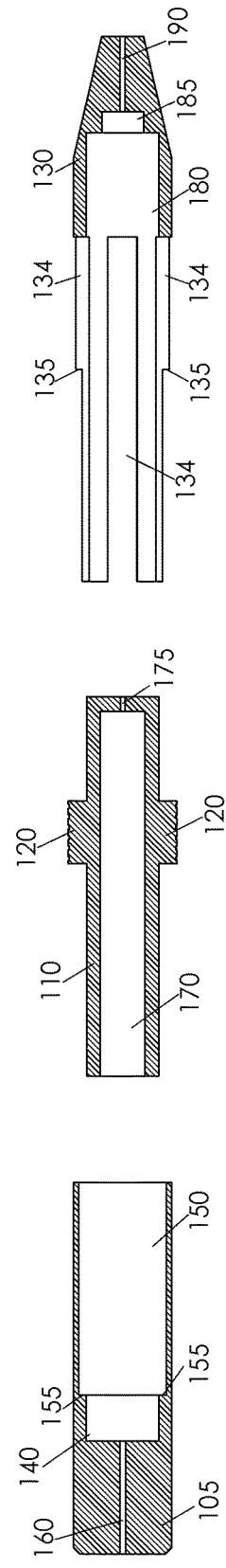
FIG. 1A
FIG. 1B

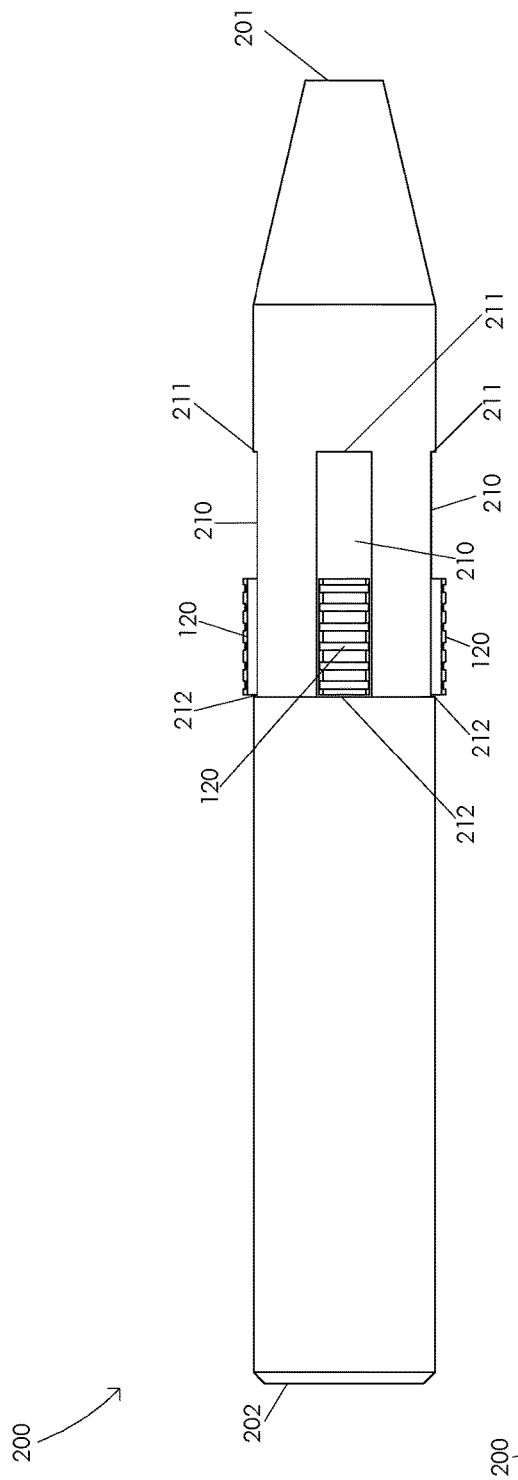
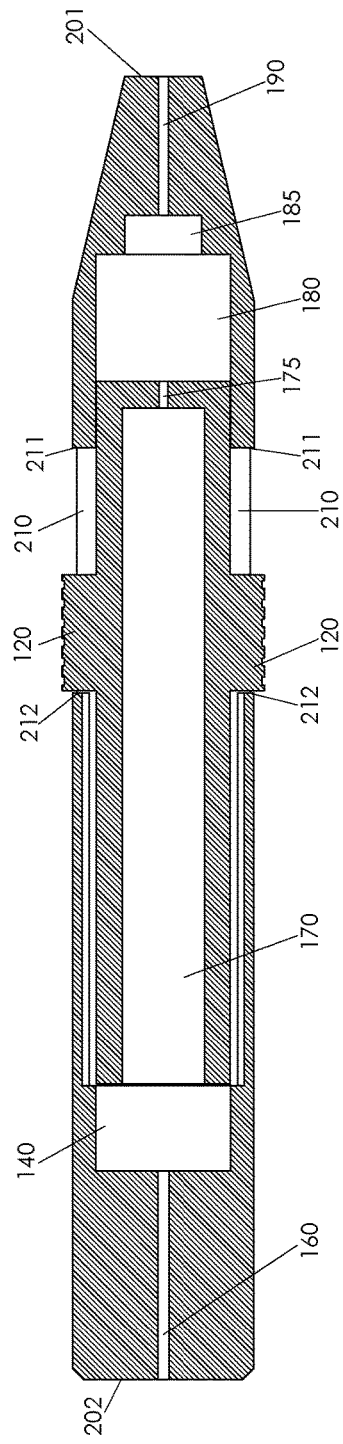
FIG. 2A
FIG. 2B

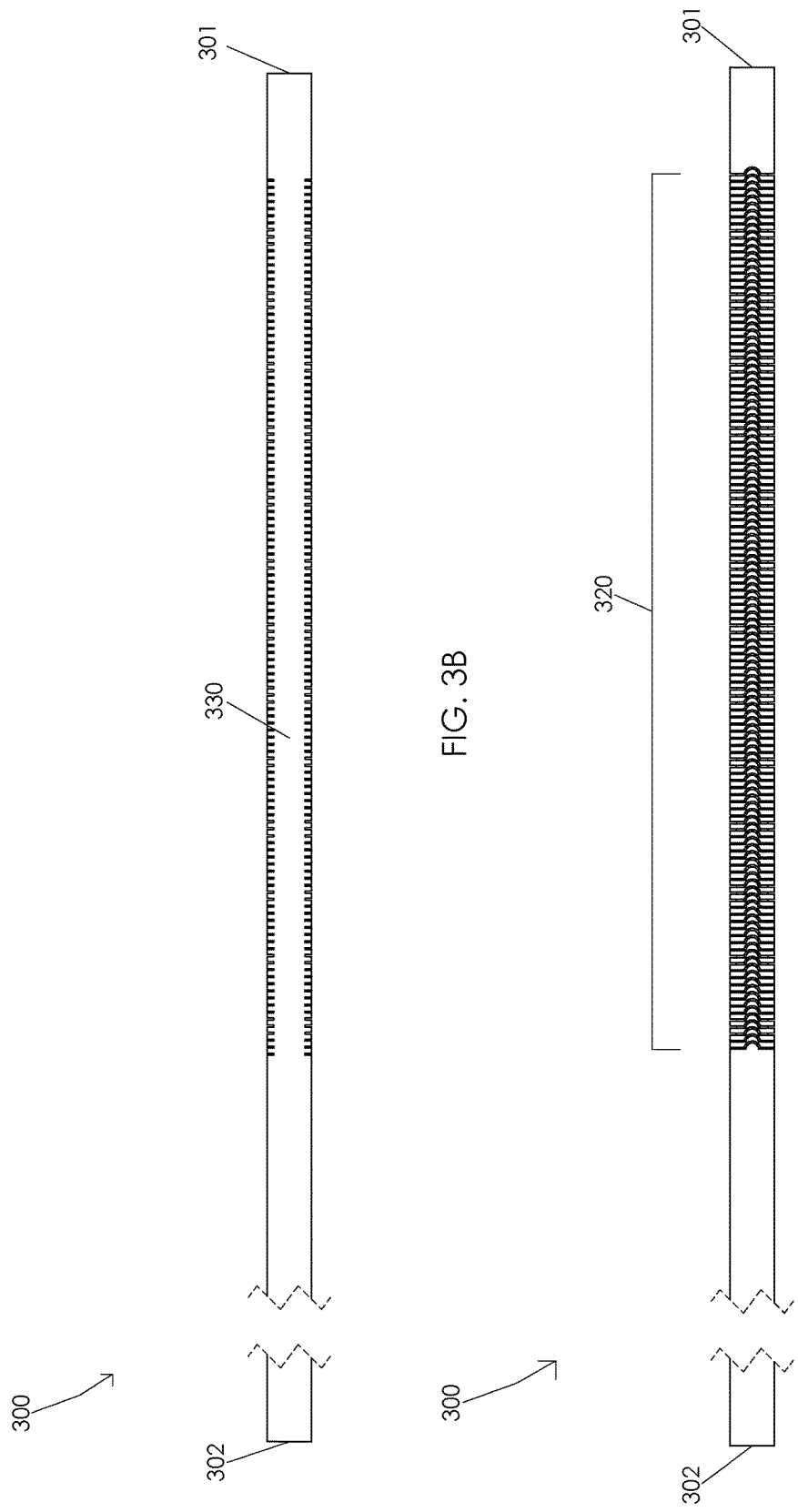

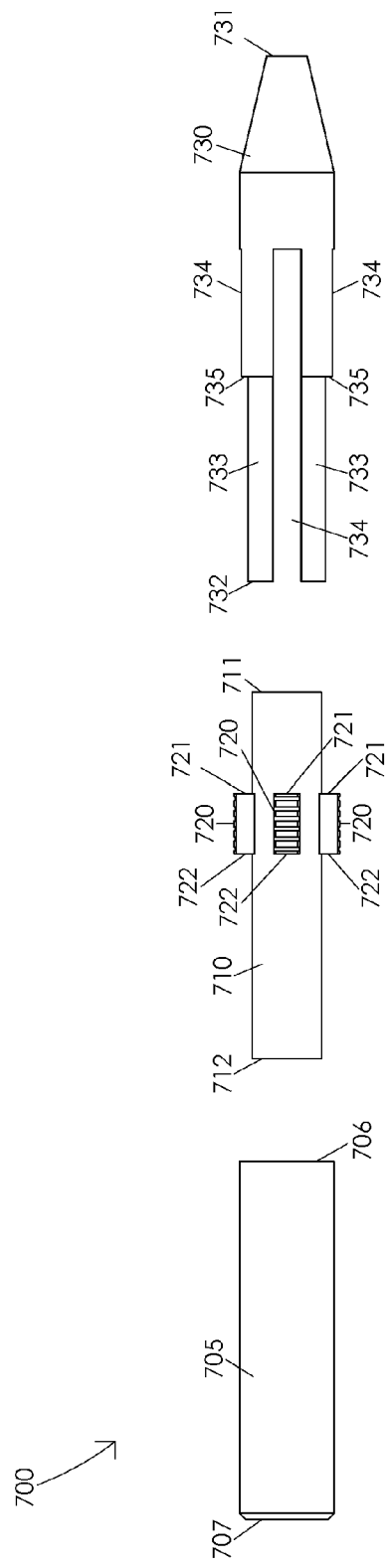
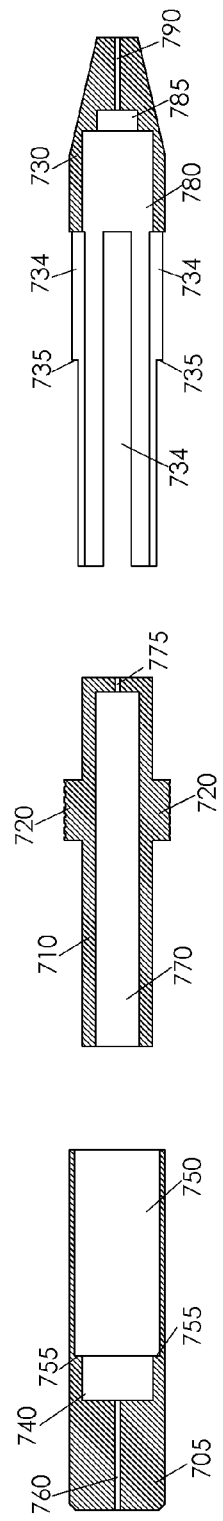
FIG. 7A
FIG. 7B

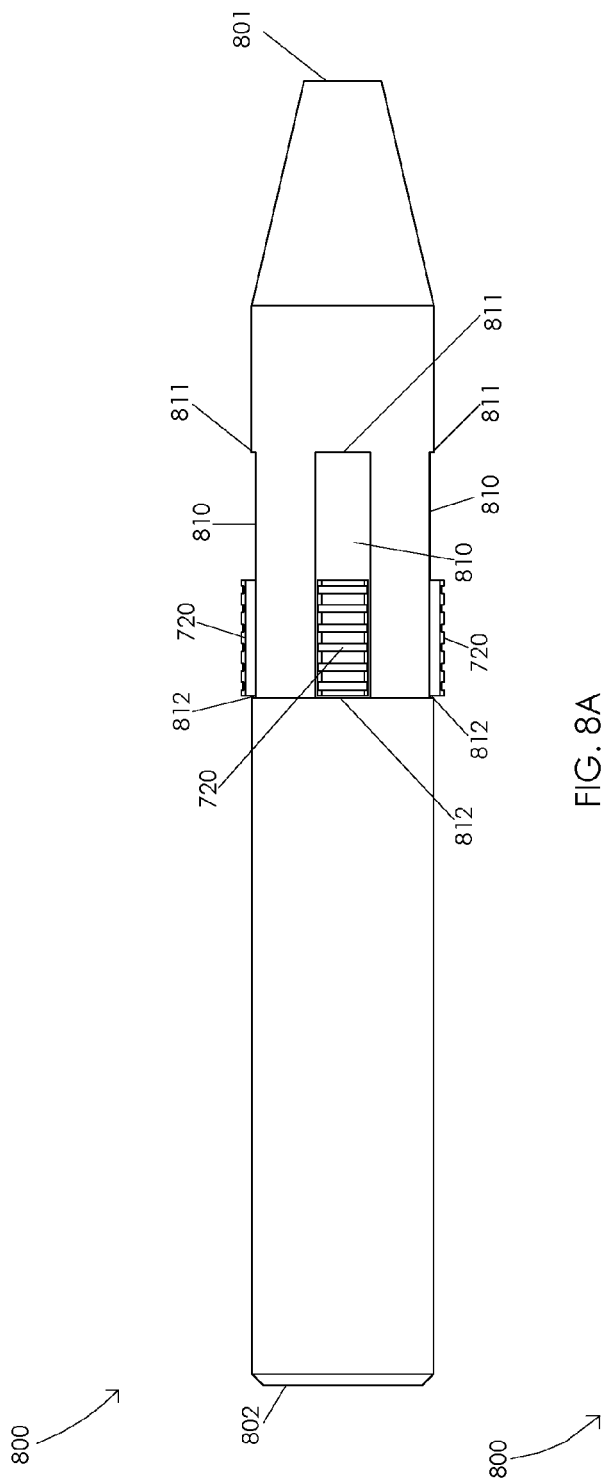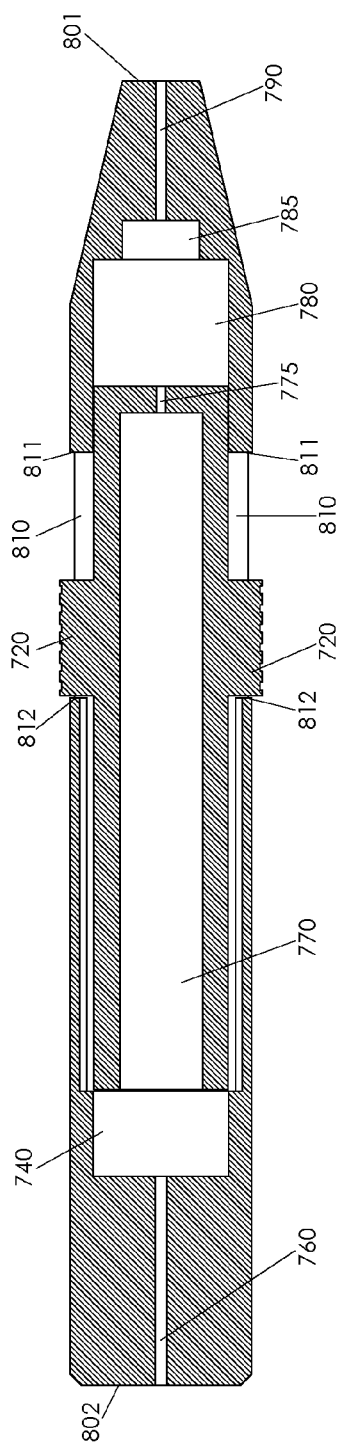

STEERABLE LASER PROBE

CROSS-REFERENCE TO RELATED APPLICATIONS

This application claims the benefit of U.S. Provisional Application No. 61/678,591, filed Aug. 1, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle having a handle distal end and a handle proximal end, a plurality of actuation controls of the handle, a housing tube having a housing tube distal end and a housing tube proximal end, and an optic fiber disposed within an inner bore of the handle and the housing tube. Illustratively, an actuation of an actuation control of the plurality of actuation controls may be configured to gradually curve the housing tube. In one or more embodiments, a gradual curving of the housing tube may be configured to gradually curve the optic fiber. Illustratively, an actuation of an actuation control of the plurality of actuation controls may be configured to gradually straighten the housing tube. In one or more embodiments, a gradual straightening of the housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating an exploded view of a handle assembly;

FIGS. 2A and 2B are schematic diagrams illustrating a handle;

FIGS. 3A, 3B, and 3C are schematic diagrams illustrating a housing tube;

FIGS. 7A and 7B are schematic diagrams illustrating an exploded view of a handle assembly;

FIGS. 8A and 8B are schematic diagrams illustrating a handle;

DETAILED DESCRIPTION OF AN ILLUSTRATIVE EMBODIMENT

Figure 3C:
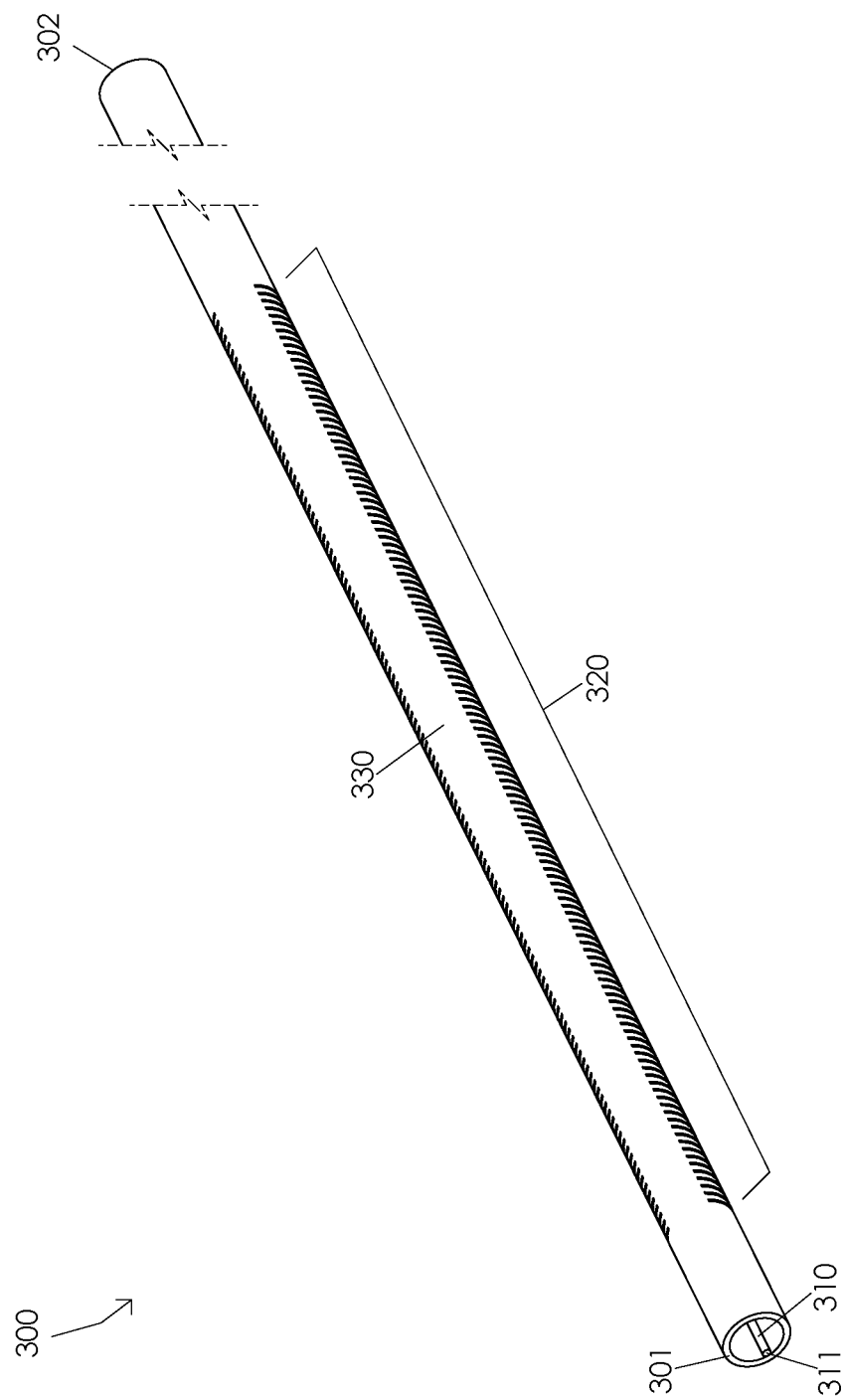

FIGS. 1A and 1B are schematic diagrams illustrating an exploded view of a handle assembly 100. FIG. 1A illustrates a side view of handle assembly 100. In one or more embodiments, handle assembly 100 may comprise a handle end cap 105 having a handle end cap distal end 106 and a handle end cap proximal end 107, an actuation mechanism 110 having an actuation mechanism distal end 111 and an actuation mechanism proximal end 112, and a handle base 130 having a handle base distal end 131 and a handle base proximal end 132. Illustratively, actuation mechanism 110 may comprise a plurality of actuation controls 120. For example, each actuation control 120 of a plurality of actuation controls 120 may comprise an actuation control distal end 121 and an actuation control proximal end 122. In one or more embodiments, handle base 130 may comprise a plurality of handle base limbs 133, a plurality of handle base channels 134, and a handle end cap interface 135.

FIG. 1B illustrates a cross-sectional view of handle assembly 100. In one or more embodiments, handle assembly 100 may comprise a proximal chamber 140, a handle base housing 150, a handle base interface 155, an optic fiber housing 160, an inner bore 170, a housing tube housing 175, an actuation mechanism guide 180, a pressure mechanism housing 185, and a housing tube guide 190. Handle end cap 105, actuation mechanism 110, actuation control 120, and handle base 130 may be manufactured from any suitable material, e.g., polymers, metals, metal alloys, etc., or from any combination of suitable materials.

FIGS. 2A and 2B are schematic diagrams illustrating a handle 200. FIG. 2A illustrates a side view of handle 200. In one or more embodiments, handle 200 may comprise a handle distal end 201, a handle proximal end 202, and a plurality of actuation control guides 210. For example, each actuation control guide 210 of a plurality of actuation control guides 210 may comprise an actuation control guide distal end 211 and an actuation control guide proximal end 212. Illustratively, handle distal end 201 may comprise handle base distal end 131. In one or more embodiments, handle proximal end 202 may comprise handle end cap proximal end 107.

FIG. 2B illustrates a cross-sectional view of handle 200. Illustratively, actuation mechanism 110 may be disposed within handle end cap 105 and handle base 130. In one or more embodiments, a portion of actuation mechanism 110 may be disposed within handle base housing 150, e.g., actuation mechanism proximal end 112 may be disposed within handle base housing 150. Illustratively, a portion of actuation mechanism 110 may be disposed within actuation mechanism guide 180, e.g., actuation mechanism distal end 111 may be disposed within actuation mechanism guide 180. In one or more embodiments, a portion of handle base 130 may be disposed within handle end cap 105, e.g., handle base proximal end 132 may be disposed within handle end cap 105. Illustratively, a portion of handle base 130 may be disposed within handle base housing 150. In one or more embodiments, a portion of handle base 130 may be disposed within handle base housing 150, e.g., handle base proximal end 132 may be configured to interface with handle base interface 155. Illustratively, a portion of handle base 130 may be disposed within handle base housing 150, e.g., handle end cap distal end 106 may be configured to interface with handle end cap interface 135. In one or more embodiments, a portion of handle base 130 may be fixed within a portion of handle end cap 105, e.g., by an adhesive or any suitable fixation means. For example, a portion of handle base 130 may be fixed within handle base housing 150, e.g., by an adhesive or any suitable fixation means.

Illustratively, each actuation control 120 of a plurality of actuation controls 120 may be disposed within an actuation control guide 210 of a plurality of actuation control guides 210. In one or more embodiments, each actuation control guide 210 of a plurality of actuation control guides 210 may comprise a handle base channel 134 of a plurality of handle base channels 134. In one or more embodiments, at least one actuation control 120 may be configured to actuate within at least one actuation control guide 210. Illustratively, each actuation control 120 of a plurality of actuation controls 120 may be configured to actuate within an actuation control guide 210 of a plurality of actuation control guides 210. In one or more embodiments, an actuation of a particular actuation control 120 in a particular actuation control guide 210 may be configured to actuate each actuation control 120 of a plurality of actuation controls 120. In one or more embodiments, actuation controls 120 may be configured to actuate within actuation control guides 210 in pairs or groups. Illustratively, an actuation of first actuation control 120 within a first actuation control guide 210 may be configured to actuate a second actuation control 120 within a second actuation control guide 210.

In one or more embodiments, actuation mechanism 110 may be configured to actuate within actuation mechanism guide 180. For example, actuation mechanism guide 180 may comprise a lubricant configured to facilitate an actuation of actuation mechanism 110 within actuation mechanism guide 180. Illustratively, an actuation of an actuation control 120 within an actuation control guide 210 may be configured to actuate actuation mechanism 110, e.g., within actuation mechanism guide 180. In one or more embodiments, an actuation of an actuation control 120 towards an actuation control guide distal end 211, e.g., and away from an actuation control guide proximal end 212, may be configured to actuate actuation mechanism 110 towards handle distal end 201, e.g., and away from handle proximal end 202. Illustratively, an actuation of an actuation control 120 towards an actuation control guide proximal end 212, e.g., and away from an actuation control guide distal end 211, may be configured to actuate actuation mechanism towards handle proximal end 202, e.g., and away from handle distal end 201.

In one or more embodiments, a surgeon may actuate actuation mechanism 110 within actuation mechanism guide 180, e.g., by manipulating an actuation control 120 of a plurality of actuation controls 120 when handle 200 is in a first rotational orientation. Illustratively, the surgeon may rotate handle 200 and actuate actuation mechanism 110 within actuation mechanism guide 180, e.g., by manipulating an actuation control 120 of a plurality of actuation controls 120 when handle 200 is in a second rotational orientation. In one or more embodiments, the surgeon may rotate handle 200 and actuate actuation mechanism 110 within actuation mechanism guide 180, e.g., by manipulating an actuation control 120 of a plurality of actuation controls 120 when handle 200 is in a third rotational orientation. Illustratively, a surgeon may actuate actuation mechanism 110 within actuation mechanism guide 180, e.g., by manipulating an actuation control 120 of a plurality of actuation controls 120 when handle 200 is in any rotational orientation of a plurality of rotational orientations.

FIGS. 3A, 3B, and 3C are schematic diagrams illustrating a housing tube 300. In one or more embodiments, housing tube 300 may comprise a housing tube distal end 301 and a housing tube proximal end 302. Housing tube 300 may be manufactured from any suitable material, e.g., polymers, metals, metal alloys, etc., or from any combination of suitable materials. FIG. 3A illustrates a housing tube 300 oriented to illustrate a first housing tube portion 320. Illustratively, first housing tube portion 320 may have a first stiffness. FIG. 3B illustrates a housing tube 300 oriented to illustrate a second housing tube portion 330. Illustratively, second housing tube portion 330 may have a second stiffness. In one or more embodiments, the second stiffness may be greater than the first stiffness. Illustratively, first housing tube portion 320 may comprise a first material having a first stiffness. In one or more embodiments, second housing tube portion 330 may comprise a second material having a second stiffness. Illustratively, the second stiffness may be greater than the first stiffness.

In one or more embodiments, housing tube 300 may comprise a non-uniform inner diameter or a non-uniform outer diameter, e.g., to vary a stiffness of one or more portions of housing tube 300. Illustratively, a first housing tube portion 320 may comprise a first inner diameter of housing tube 300 and a second housing tube portion 330 may comprise a second inner diameter of housing tube 300. In one or more embodiments, the first inner diameter of housing tube 300 may be larger than the second inner diameter of housing tube 300. Illustratively, a first housing tube portion 320 may comprise a first outer diameter of housing tube 300 and a second housing tube portion 330 may comprise a second outer diameter of housing tube 300. In one or more embodiments, the first outer diameter of housing tube 300 may be smaller than the second outer diameter of housing tube 300.

In one or more embodiments, first housing tube portion 320 may comprise one or more apertures configured to produce a first stiffness of first housing tube portion 320. Illustratively, second housing tube portion 330 may comprise a solid portion of housing tube 300 having a second stiffness. In one or more embodiments, the second stiffness may be greater than the first stiffness. Illustratively, first housing tube portion 320 may comprise one or more apertures configured to produce a first stiffness of first housing tube portion 320. In one or more embodiments, second housing tube portion 330 may comprise one or more apertures configured to produce a second stiffness of second housing tube portion 330. Illustratively, the second stiffness may be greater than the first stiffness.

In one or more embodiments, first housing tube portion 320 may comprise a plurality of slits configured to separate one or more solid portions of housing tube 300. Illustratively, a plurality of slits may be cut, e.g., laser cut, into first housing tube portion 320. In one or more embodiments, first housing tube portion 320 may comprise a plurality of slits configured to minimize a force of friction between housing tube 300 and a cannula, e.g., as housing tube 300 is inserted into the cannula or as housing tube 300 is extracted from the cannula. For example, each slit of the plurality of slits may comprise one or more arches configured to minimize a force of friction between housing tube 300 and a cannula.

FIG. 3C illustrates an angled view of housing tube 300. Illustratively, an optic fiber 310 may be disposed within housing tube 300. In one or more embodiments, optic fiber 310 may comprise an optic fiber distal end 311 and an optic fiber proximal end 312. Illustratively, optic fiber 310 may be configured to transmit light, e.g., laser light, illumination light, etc. In one or more embodiments, optic fiber 310 may be disposed within housing tube 300 wherein optic fiber distal end 311 is adjacent to housing tube distal end 301. Illustratively, optic fiber 310 may be disposed within housing tube 300 wherein a portion of optic fiber 310 may be adjacent to a portion of first housing tube portion 320. In one or more embodiments, a portion of optic fiber 310 may be fixed to an inner portion of housing tube 300, e.g., by an adhesive or any suitable fixation means.

Figure 4:
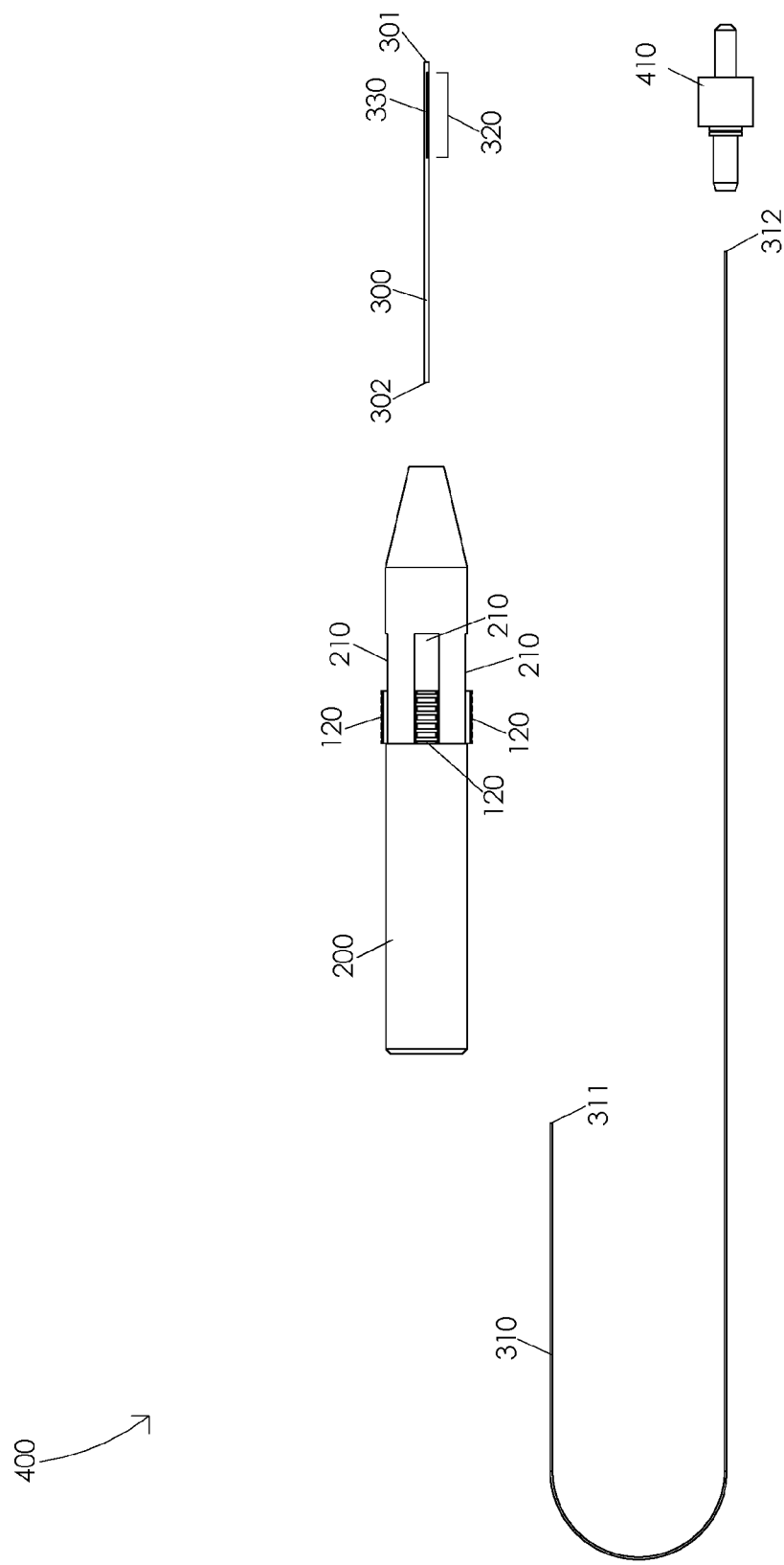
FIG. 4 is a schematic diagram illustrating an exploded view of a steerable laser probe assembly.

FIG. 4 is a schematic diagram illustrating an exploded view of a steerable laser probe assembly 400. In one or more embodiments, steerable laser probe assembly 400 may comprise a handle 200, a housing tube 300 having a housing tube distal end 301 and a housing tube proximal end 302, an optic fiber 310 having an optic fiber distal end 311 and an optic fiber proximal end 312, and a light source interface 410. Illustratively, light source interface 410 may be configured to interface with optic fiber 310, e.g., at optic fiber proximal end 312. In one or more embodiments, light source interface 410 may comprise a standard light source connecter, e.g., an SMA connector.

Illustratively, a portion of housing tube 300 may be fixed to actuation mechanism 110, e.g., housing tube proximal end 302 may be fixed to actuation mechanism distal end 111. In one or more embodiments, a portion of housing tube 300 may be fixed to actuation mechanism 110, e.g., by an adhesive or any suitable fixation means. Illustratively, a portion of housing tube 300 may be disposed within actuation mechanism 110, e.g., housing tube proximal end 302 may be disposed within housing tube housing 175. In one or more embodiments, a portion of housing tube 300 may be fixed within housing tube housing 175, e.g., by an adhesive or any suitable fixation means. Illustratively, housing tube 300 may be disposed within actuation mechanism guide 180 and housing tube guide 190. In one or more embodiments, a portion of housing tube 300 may extend from handle distal end 201, e.g., housing tube distal end 301 may extend from handle distal end 201.

Illustratively, optic fiber 310 may be disposed within optic fiber housing 160, proximal chamber 140, inner bore 170, housing tube housing 175, housing tube 300, actuation mechanism guide 180, and housing tube guide 190. In one or more embodiments, a portion of optic fiber 310 may be fixed to a portion of housing tube 300, e.g., by an adhesive or any suitable fixation means. Illustratively, a portion of optic fiber 310 may be fixed in a position relative to handle 200. In one or more embodiments, a portion of optic fiber 310 may be fixed within optic fiber housing 160, e.g., by an adhesive or any suitable fixation means. Illustratively, a portion of optic fiber 310 may be fixed within optic fiber housing 160, e.g., by a press fit or any suitable fixation means. In one or more embodiments, a portion of optic fiber 310 may be fixed to a portion of housing tube 300 and a portion of optic fiber 310 may be fixed in a position relative to handle 200.

Illustratively, an actuation of an actuation control 120 within an actuation control guide 210, e.g., towards actuation control guide distal end 211 and away from actuation control guide proximal end 212, may be configured to actuate actuation mechanism 110 within actuation mechanism guide 180, e.g., towards handle distal end 201 and away from handle proximal end 202. In one or more embodiments, an actuation of actuation mechanism 110 towards handle distal end 201 and away from handle proximal end 202 may be configured to extend actuation mechanism 110 relative to optic fiber 310. Illustratively, an extension of actuation mechanism 110 relative to optic fiber 310 may be configured to extend housing tube 300 relative to optic fiber 310. In one or more embodiments, optic fiber 310 may be configured to resist an extension of housing tube 300 relative to optic fiber 310. Illustratively, optic fiber 310 may be configured to resist an extension of housing tube 300 relative to optic fiber 310, e.g., a portion of optic fiber 310 may be configured to apply a force to a portion of housing tube 300. In one or more embodiments, an application of a force, e.g., a resistive force, to a portion of housing tube 300 may be configured to compress a portion of housing tube 300 causing housing tube 300 to gradually curve. For example, an application of a force to a portion of housing tube 300 may be configured to compress first housing tube portion 320 causing housing tube 300 to gradually curve. Illustratively, a gradual curving of housing tube 300 may be configured to gradually curve optic fiber 310. In one or more embodiments, an actuation of an actuation control 120 within an actuation control guide 210, e.g., towards actuation control guide distal end 211 and away from actuation control guide proximal end 212, may be configured to gradually curve optic fiber 310.

Illustratively, an actuation of an actuation control 120 within an actuation control guide 210, e.g., towards actuation control guide proximal end 212 and away from actuation control guide distal end 211, may be configured to actuate actuation mechanism 110 within actuation mechanism guide 180, e.g., towards handle proximal end 202 and away from handle distal end 201. In one or more embodiments, an actuation of actuation mechanism 110 towards handle proximal end 202 and away from handle distal end 201 may be configured to retract actuation mechanism 110 relative to optic fiber 310. Illustratively, a retraction of actuation mechanism 110 relative to optic fiber 310 may be configured to retract housing tube 300 relative to optic fiber 310. In one or more embodiments, optic fiber 310 may be configured to facilitate a retraction of housing tube 300 relative to optic fiber 310. Illustratively, optic fiber 310 may be configured to facilitate a refraction of housing tube 300 relative to optic fiber 310, e.g., a portion of optic fiber 310 may be configured to reduce a force applied to a portion of housing tube 300. In one or more embodiments, a reduction of a force, e.g., a resistive force, applied to a portion of housing tube 300 may be configured to decompress a portion of housing tube 300 causing housing tube 300 to gradually straighten. For example, a reduction of a force applied to a portion of housing tube 300 may be configured to decompress first housing tube portion 320 causing housing tube 300 to gradually straighten. Illustratively, a gradual straightening of housing tube 300 may be configured to gradually straighten optic fiber 310. In one or more embodiments, an actuation of an actuation control 120 within an actuation control guide 210, e.g., towards actuation control guide proximal end 212 and away from actuation control guide distal end 211, may be configured to gradually straighten optic fiber 310.

Figure 5A:
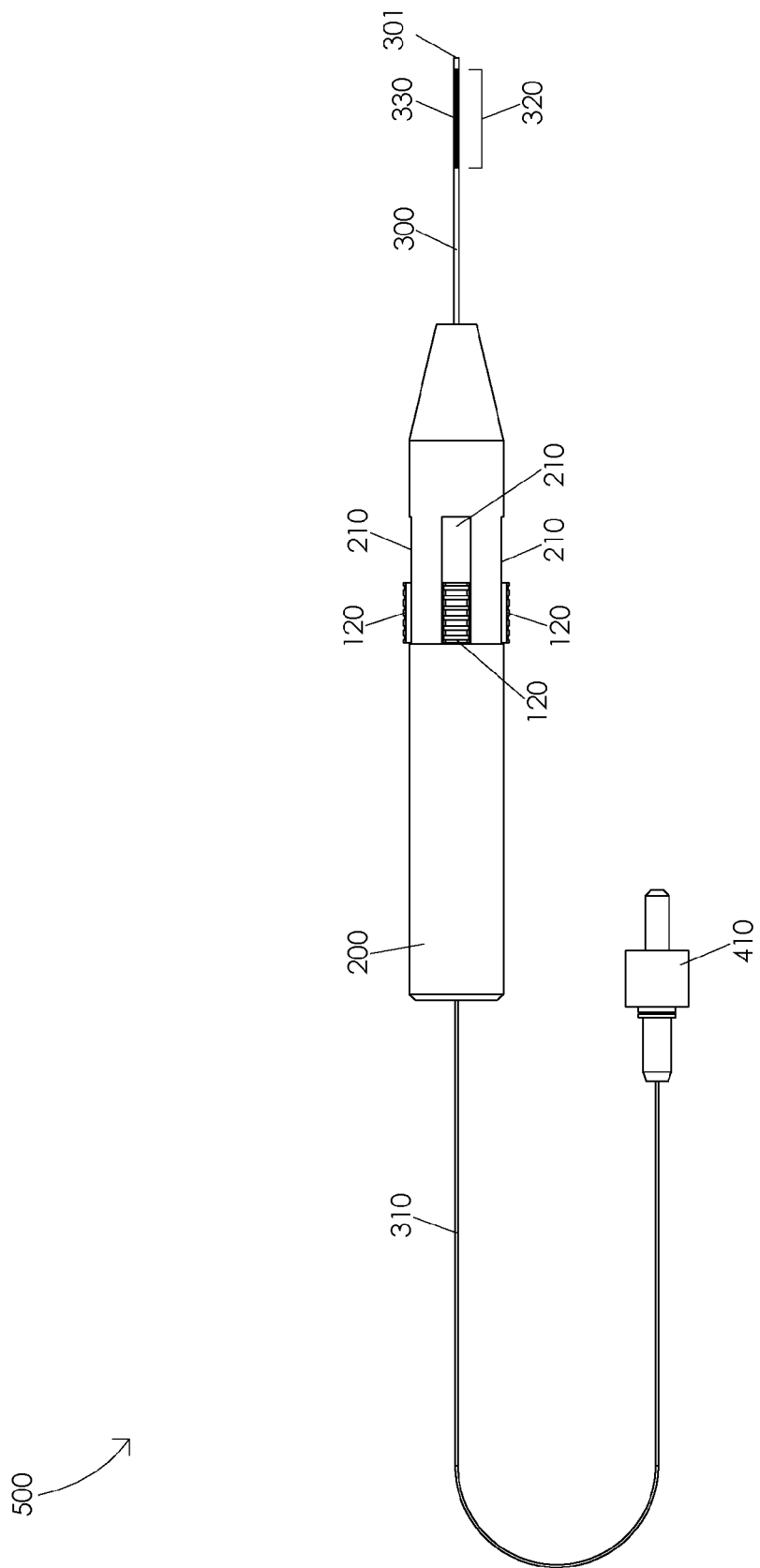
FIGS. 5A, 5B, 5C, 5D, and 5E are schematic diagrams illustrating a gradual curving of an optic fiber.

FIGS. 5A, 5B, 5C, 5D, and 5E are schematic diagrams illustrating a gradual curving of an optic fiber 310. FIG. 5A illustrates a straight optic fiber 500. In one or more embodiments, optic fiber 310 may comprise a straight optic fiber 500, e.g., when housing tube 300 is fully retracted relative to handle proximal end 202. Illustratively, optic fiber 310 may comprise a straight optic fiber 500, e.g., when an actuation control 120 of a plurality of actuation controls 120 is fully retracted relative to an actuation control guide proximal end 212. In one or more embodiments, optic fiber 310 may comprise a straight optic fiber 500, e.g., when actuation mechanism 110 is fully refracted relative to handle proximal end 202. For example, optic fiber 310 may comprise a straight optic fiber 500, e.g., when first housing tube portion 320 is fully decompressed. Illustratively, a line tangent to optic fiber distal end 311 may be parallel to a line tangent to housing tube proximal end 302, e.g., when optic fiber 310 comprises a straight optic fiber 500.

Figure 5B:
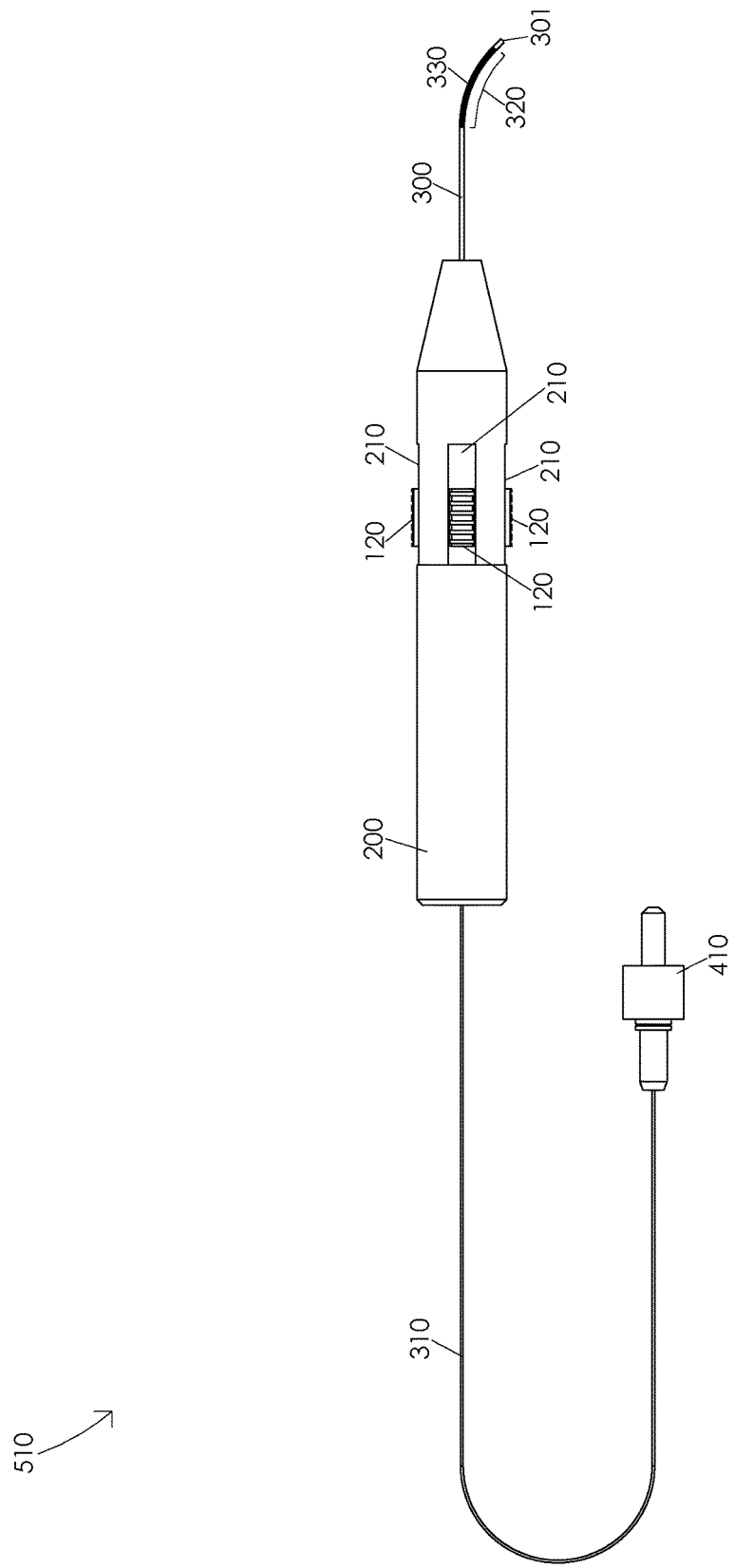

FIG. 5B illustrates an optic fiber in a first curved position 510. In one or more embodiments, an actuation of an actuation control 120 within an actuation control guide 210, e.g., towards actuation control guide distal end 211 and away from actuation control guide proximal end 212, may be configured to gradually curve optic fiber 310 from a straight optic fiber 500 to an optic fiber in a first curved position 510. Illustratively, an actuation of an actuation control 120 within an actuation control guide 210, e.g., towards actuation control guide distal end 211 and away from actuation control guide proximal end 212, may be configured to extend actuation mechanism 110 relative to optic fiber 310. In one or more embodiments, an extension of actuation mechanism 110 relative to optic fiber 310 may be configured to extend housing tube 300 relative to optic fiber 310. Illustratively, a portion of optic fiber 310, e.g., a portion of optic fiber 310 fixed to a portion of housing tube 300, may be configured to resist an extension of housing tube 300 relative to optic fiber 310. In one or more embodiments, an extension of housing tube 300 relative to optic fiber 310 may be configured to apply a force to a portion of housing tube 300. Illustratively, an application of a force to a portion of housing tube 300 may be configured to cause housing tube 300 to gradually curve, e.g., by compressing a portion of housing tube 300. For example, an application of a force to a portion of housing tube 300 may be configured to compress first housing tube portion 320 causing housing tube 300 to gradually curve. In one or more embodiments, a gradual curving of housing tube 300 may be configured to gradually curve optic fiber 310, e.g., from a straight optic fiber 500 to an optic fiber in a first curved position 510. In one or more embodiments, a line tangent to optic fiber distal end 311 may intersect a line tangent to housing tube proximal end 302 at a first angle, e.g., when optic fiber 310 comprises an optic fiber in a first curved position 510. Illustratively, the first angle may comprise any angle greater than zero degrees. For example, the first angle may comprise a 45 degree angle.

Figure 5C:
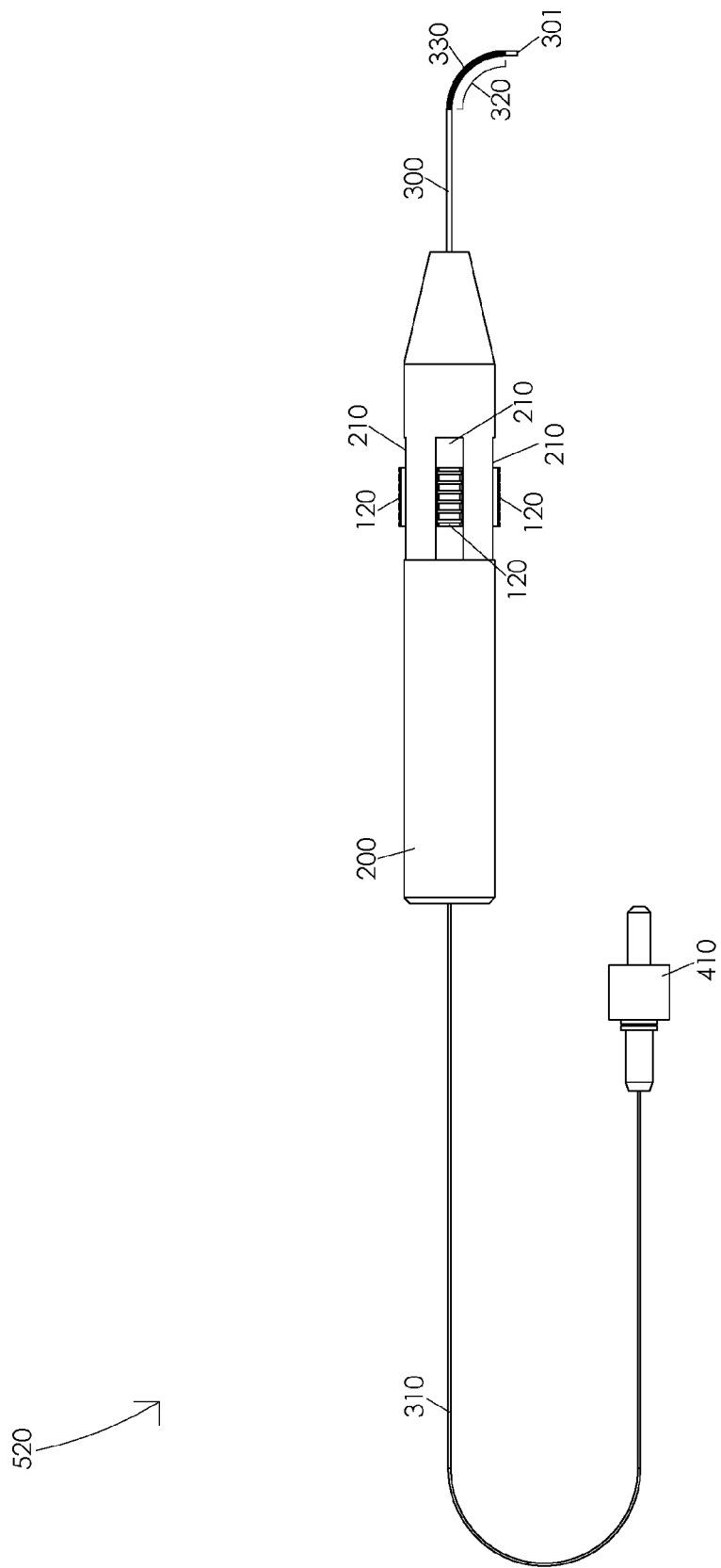

FIG. 5C illustrates an optic fiber in a second curved position 520. In one or more embodiments, an actuation of an actuation control 120 within an actuation control guide 210, e.g., towards actuation control guide distal end 211 and away from actuation control guide proximal end 212, may be configured to gradually curve optic fiber 310 from an optic fiber in a first curved position 510 to an optic fiber in a second curved position 520. Illustratively, an actuation of an actuation control 120 within an actuation control guide 210, e.g., towards actuation control guide distal end 211 and away from actuation control guide proximal end 212, may be configured to extend actuation mechanism 110 relative to optic fiber 310. In one or more embodiments, an extension of actuation mechanism 110 relative to optic fiber 310 may be configured to extend housing tube 300 relative to optic fiber 310. Illustratively, a portion of optic fiber 310, e.g., a portion of optic fiber 310 fixed to a portion of housing tube 300, may be configured to resist an extension of housing tube 300 relative to optic fiber 310. In one or more embodiments, an extension of housing tube 300 relative to optic fiber 310 may be configured to apply a force to a portion of housing tube 300. Illustratively, an application of a force to a portion of housing tube 300 may be configured to cause housing tube 300 to gradually curve, e.g., by compressing a portion of housing tube 300. For example, an application of a force to a portion of housing tube 300 may be configured to compress first housing tube portion 320 causing housing tube 300 to gradually curve. In one or more embodiments, a gradual curving of housing tube 300 may be configured to gradually curve optic fiber 310, e.g., from an optic fiber in a first curved position 510 to an optic fiber in a second curved position 520. In one or more embodiments, a line tangent to optic fiber distal end 311 may intersect a line tangent to housing tube proximal end 302 at a second angle, e.g., when optic fiber 310 comprises an optic fiber in a second curved position 520. Illustratively, the second angle may comprise any angle greater than the first angle. For example, the second angle may comprise a 90 degree angle.

Figure 5D:
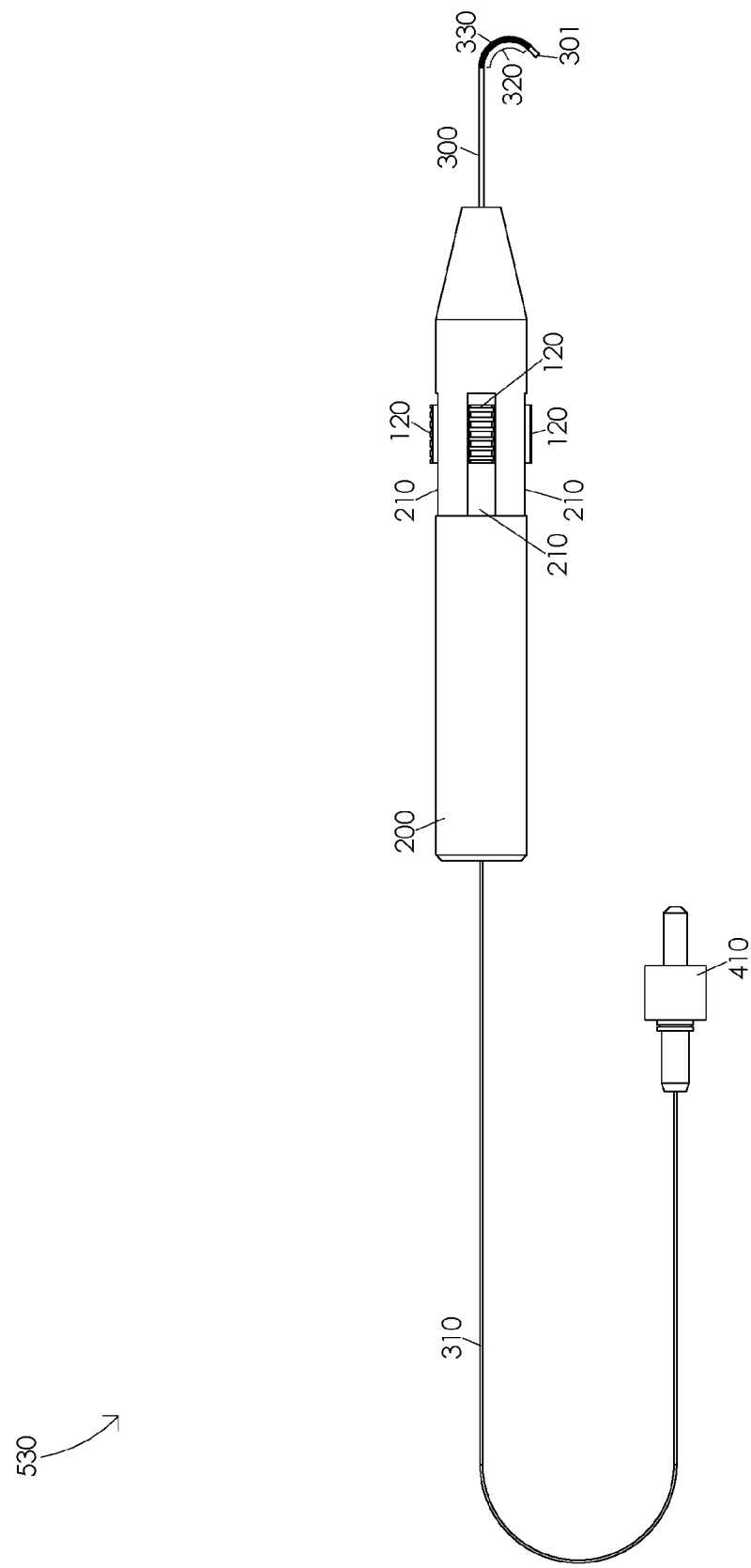

FIG. 5D illustrates an optic fiber in a third curved position 530. In one or more embodiments, an actuation of an actuation control 120 within an actuation control guide 210, e.g., towards actuation control guide distal end 211 and away from actuation control guide proximal end 212, may be configured to gradually curve optic fiber 310 from an optic fiber in a second curved position 520 to an optic fiber in a third curved position 530. Illustratively, an actuation of an actuation control 120 within an actuation control guide 210, e.g., towards actuation control guide distal end 211 and away from actuation control guide proximal end 212, may be configured to extend actuation mechanism 110 relative to optic fiber 310. In one or more embodiments, an extension of actuation mechanism 110 relative to optic fiber 310 may be configured to extend housing tube 300 relative to optic fiber 310. Illustratively, a portion of optic fiber 310, e.g., a portion of optic fiber 310 fixed to a portion of housing tube 300, may be configured to resist an extension of housing tube 300 relative to optic fiber 310. In one or more embodiments, an extension of housing tube 300 relative to optic fiber 310 may be configured to apply a force to a portion of housing tube 300. Illustratively, an application of a force to a portion of housing tube 300 may be configured to cause housing tube 300 to gradually curve, e.g., by compressing a portion of housing tube 300. For example, an application of a force to a portion of housing tube 300 may be configured to compress first housing tube portion 320 causing housing tube 300 to gradually curve. In one or more embodiments, a gradual curving of housing tube 300 may be configured to gradually curve optic fiber 310, e.g., from an optic fiber in a second curved position 520 to an optic fiber in a third curved position 530. In one or more embodiments, a line tangent to optic fiber distal end 311 may intersect a line tangent to housing tube proximal end 302 at a third angle, e.g., when optic fiber 310 comprises an optic fiber in a third curved position 530. Illustratively, the third angle may comprise any angle greater than the second angle. For example, the third angle may comprise a 135 degree angle.

Figure 5E:
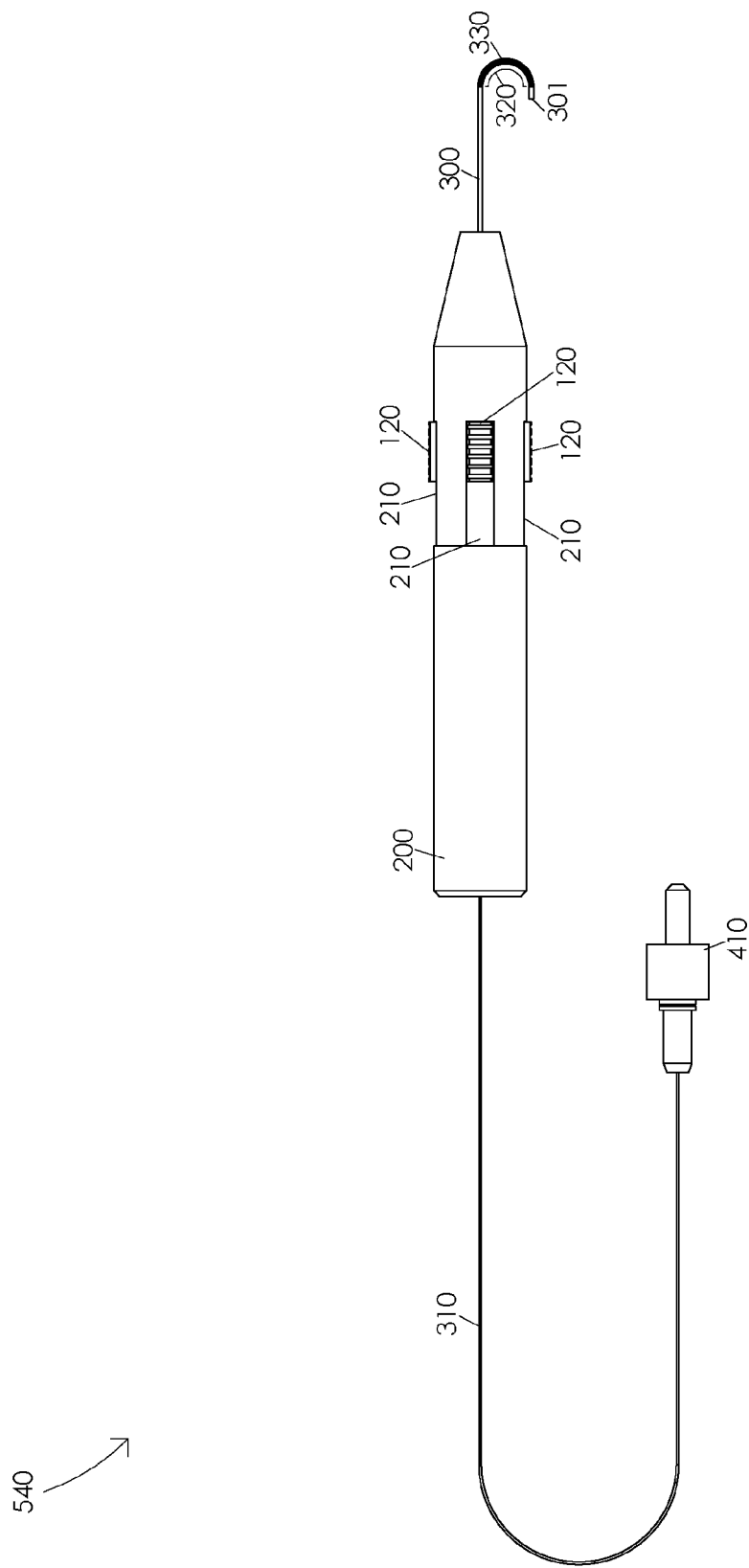

FIG. 5E illustrates an optic fiber in a fourth curved position 540. In one or more embodiments, an actuation of an actuation control 120 within an actuation control guide 210, e.g., towards actuation control guide distal end 211 and away from actuation control guide proximal end 212, may be configured to gradually curve optic fiber 310 from an optic fiber in a third curved position 530 to an optic fiber in a fourth curved position 540. Illustratively, an actuation of an actuation control 120 within an actuation control guide 210, e.g., towards actuation control guide distal end 211 and away from actuation control guide proximal end 212, may be configured to extend actuation mechanism 110 relative to optic fiber 310. In one or more embodiments, an extension of actuation mechanism 110 relative to optic fiber 310 may be configured to extend housing tube 300 relative to optic fiber 310. Illustratively, a portion of optic fiber 310, e.g., a portion of optic fiber 310 fixed to a portion of housing tube 300, may be configured to resist an extension of housing tube 300 relative to optic fiber 310. In one or more embodiments, an extension of housing tube 300 relative to optic fiber 310 may be configured to apply a force to a portion of housing tube 300. Illustratively, an application of a force to a portion of housing tube 300 may be configured to cause housing tube 300 to gradually curve, e.g., by compressing a portion of housing tube 300. For example, an application of a force to a portion of housing tube 300 may be configured to compress first housing tube portion 320 causing housing tube 300 to gradually curve. In one or more embodiments, a gradual curving of housing tube 300 may be configured to gradually curve optic fiber 310, e.g., from an optic fiber in a third curved position 530 to an optic fiber in a fourth curved position 540. In one or more embodiments, a line tangent to optic fiber distal end 311 may be parallel to a line tangent to housing tube proximal end 302, e.g., when optic fiber 310 comprises an optic fiber in a fourth curved position 540.

In one or more embodiments, one or more properties of a steerable laser probe may be adjusted to attain one or more desired steerable laser probe features. Illustratively, a length that housing tube distal end 301 extends from actuation mechanism distal end 111 may be adjusted to vary an amount of actuation of an actuation control 120 of a plurality of actuation controls 120 configured to curve housing tube 300 to a particular curved position. In one or more embodiments, a stiffness of first housing tube portion 320 or a stiffness of second housing tube portion 330 may be adjusted to vary an amount of actuation of an actuation control 120 of a plurality of actuation controls 120 configured to curve housing tube 300 to a particular curved position. Illustratively, a material comprising first housing tube portion 320 or a material comprising second housing tube portion 330 may be adjusted to vary an amount of actuation of an actuation control 120 of a plurality of actuation controls 120 configured to curve housing tube 300 to a particular curved position.

In one or more embodiments, a number of apertures in housing tube 300 may be adjusted to vary an amount of actuation of an actuation control 120 of a plurality of actuation controls 120 configured to curve housing tube 300 to a particular curved position. Illustratively, a location of one or more apertures in housing tube 300 may be adjusted to vary an amount of actuation of an actuation control 120 of a plurality of actuation controls 120 configured to curve housing tube 300 to a particular curved position. In one or more embodiments, a geometry of one or more apertures in housing tube 300 may be adjusted to vary an amount of actuation of an actuation control 120 of a plurality of actuation controls 120 configured to curve housing tube 300 to a particular curved position. Illustratively, a geometry of one or more apertures in housing tube 300 may be uniform, e.g., each aperture of the one or more apertures may have a same geometry. In one or more embodiments, a geometry of one or more apertures in housing tube 300 may be non-uniform, e.g., a first aperture in housing tube 300 may have a first geometry and a second aperture in housing tube 300 may have a second geometry. Illustratively, a geometry or location of one or more apertures in housing tube 300 may be optimized to evenly distribute an applied force. For example, a geometry or location of one or more apertures in housing tube 300 may be optimized to evenly distribute a compressive force applied to first housing tube portion 320.

Illustratively, a stiffness of first housing tube portion 320 or a stiffness of second housing tube portion 330 may be adjusted to vary a bend radius of housing tube 300. In one or more embodiments, a stiffness of first housing tube portion 320 or a stiffness of second housing tube portion 330 may be adjusted to vary a radius of curvature of housing tube 300, e.g., when housing tube 300 is in a particular curved position. Illustratively, a number of apertures in housing tube 300 may be adjusted to vary a bend radius of housing tube 300. In one or more embodiments, a number of apertures in housing tube 300 may be adjusted to vary a radius of curvature of housing tube 300, e.g., when housing tube 300 is in a particular curved position. Illustratively, a location or a geometry of one or more apertures in housing tube 300 may be adjusted to vary a bend radius of housing tube 300. In one or more embodiments, a location or a geometry of one or more apertures in housing tube 300 may be adjusted to vary a radius of curvature of housing tube 300, e.g., when housing tube 300 is in a particular curved position.

In one or more embodiments, a geometry of actuation mechanism 110 may be adjusted to vary an amount of actuation of an actuation control 120 of a plurality of actuation controls 120 configured to curve housing tube 300 to a particular curved position. Illustratively, a geometry of actuation mechanism guide 180 may be adjusted to vary an amount of actuation of an actuation control 120 of a plurality of actuation controls 120 configured to curve housing tube 300 to a particular curved position. In one or more embodiments, a geometry of handle end cap 105 or a geometry of handle base 130 may be adjusted to vary an amount of actuation of an actuation control 120 of a plurality of actuation controls 120 configured to curve housing tube 300 to a particular curved position. Illustratively, one or more locations within housing tube 300 wherein optic fiber 310 may be fixed to a portion of housing tube 300 may be adjusted to vary an amount of actuation of an actuation control 120 of a plurality of actuation controls 120 configured to curve housing tube 300 to a particular curved position.

In one or more embodiments, at least a portion of optic fiber 310 may be enclosed in an optic fiber sleeve configured to, e.g., protect optic fiber 310, vary a stiffness of optic fiber 310, vary an optical property of optic fiber 310, etc. Illustratively, an optic fiber sleeve may be configured to compress a portion of housing tube 300. For example, an optic fiber sleeve may enclose a portion of optic fiber 310 and the optic fiber sleeve may be fixed in a position relative to handle 200, e.g., the optic fiber sleeve may be fixed within optic fiber housing 160 by an adhesive or any suitable fixation means. Illustratively, a portion of the optic fiber sleeve may be fixed to a portion of housing tube 300, e.g., by an adhesive or any suitable fixation means. In one or more embodiments, an actuation of an actuation control 120 of a plurality of actuation controls 120 may be configured to extend housing tube 300 relative to an optic fiber sleeve. Illustratively, an extension of housing tube 300 relative to an optic fiber sleeve may be configured to cause the optic fiber sleeve to apply a force, e.g., a compressive force, to a portion of housing tube 300 causing housing tube 300 to gradually curve. In one or more embodiments, a gradual curving of housing tube 300 may be configured to gradually curve optic fiber 310.

Illustratively, optic fiber 310 may comprise a buffer, a cladding disposed in the buffer, and a core disposed in the cladding. In one or more embodiments, at least a portion of optic fiber 310 may comprise a buffer configured to protect an optical property of optic fiber 310. Illustratively, at least a portion of optic fiber 310 may comprise a buffer configured to protect an optical layer of optic fiber 310, e.g., the buffer may protect an optical layer of a curved portion of optic fiber 310. In one or more embodiments, at least a portion of optic fiber 310 may comprise a polyimide buffer configured to protect an optical property of optic fiber 310. For example, at least a portion of optic fiber 310 may comprise a Kapton buffer configured to protect an optical property of optic fiber 310.

Illustratively, a steerable laser probe may be configured to indicate, e.g., to a surgeon, a direction that optic fiber 310 may curve, e.g., due to an actuation of an actuation control 120 of a plurality of actuation controls 120. In one or more embodiments, a portion of a steerable laser probe, e.g., handle 200, may be marked in a manner configured to indicate a direction that optic fiber 310 may curve. For example, a portion of housing tube 300 may comprise a mark configured to indicate a direction that optic fiber 310 may curve. Illustratively, housing tube 300 may comprise a slight curve, e.g., a curve less than 7.5 degrees, when an actuation control 120 of a plurality of actuation controls 120 is fully retracted relative to an actuation control guide proximal end 212. In one or more embodiments, housing tube 300 may comprise a slight curve configured to indicate a direction that optic fiber 310 may curve, e.g., due to an extension of an actuation control 120 of a plurality of actuation controls 120 relative to an actuation control guide proximal end 212.

In one or more embodiments, a steerable laser probe may comprise a pressure mechanism configured to provide a force. Illustratively, a pressure mechanism may be disposed within pressure mechanism housing 185. For example, a pressure mechanism may be disposed within proximal chamber 140. In one or more embodiments, a pressure mechanism may be configured to provide a constant force. Illustratively, a pressure mechanism may be configured to provide a variable force. In one or more embodiments, a pressure mechanism may be configured to provide a resistive force, e.g., to resist an extension of actuation mechanism 110 relative to handle proximal end 202. Illustratively, a pressure mechanism may be configured to provide a facilitating force, e.g., to facilitate a retraction of actuation mechanism 110 relative to handle proximal end 202. In one or more embodiments, a pressure mechanism may be configured to provide a resistive force, e.g., to resist a retraction of actuation mechanism 110 relative to handle proximal end 202. Illustratively, a pressure mechanism may be configured to provide a facilitating force, e.g., to facilitate an extension of actuation mechanism 110 relative to handle proximal end 202. In one or more embodiments, a pressure mechanism may comprise a spring or a coil. Illustratively, a pressure mechanism may comprise a pneumatic system or any system configured to provide a force.

In one or more embodiments, one or more actuation controls 120 may be fixed together. For example, a first actuation control 120 may be connected to a second actuation control 120 wherein an actuation of the first actuation control 120 is configured to actuate the second actuation control 120 and an actuation of the second actuation control 120 is configured to actuate the first actuation control 120. Illustratively, each actuation control 120 of a plurality of actuation controls 120 may be connected wherein an actuation of a particular actuation control 120 is configured to actuate each actuation control 120 of the plurality of actuation controls 120. In one or more embodiments, each actuation control 120 may be connected to another actuation control 120 of a plurality of actuation controls 120, e.g., by a ring or any suitable structure wherein a surgeon may actuate each actuation control 120 of the plurality of actuation controls 120 in any rotational orientation of handle 200.

Illustratively, handle 200 may comprise one or more detents configured to temporarily house an actuation control 120 of a plurality of actuation controls 120. In one or more embodiments, an actuation control guide 210 may comprise one or more detents configured to temporarily fix an actuation control 120 in a position relative to handle proximal end 202. Illustratively, a surgeon may actuate an actuation control 120 of a plurality of actuation controls 120 into a detent of an actuation control guide 210, e.g., to temporarily fix an actuation control 120 in a position relative to handle proximal end 202. In one or more embodiments, temporarily fixing an actuation control 120 of a plurality of actuation controls 120 in a position relative to handle proximal end 202 may be configured to temporarily fix housing tube 300 in a particular curved position. Illustratively, a surgeon may actuate an actuation control 120 out from a detent of an actuation control guide 210, e.g., to adjust an amount of actuation of an actuation control 120 relative to handle proximal end 202. In one or more embodiments, adjusting an amount of actuation of an actuation control 120 relative to handle proximal end 202 may be configured to adjust a curvature of housing tube 300.

Figure 6A:
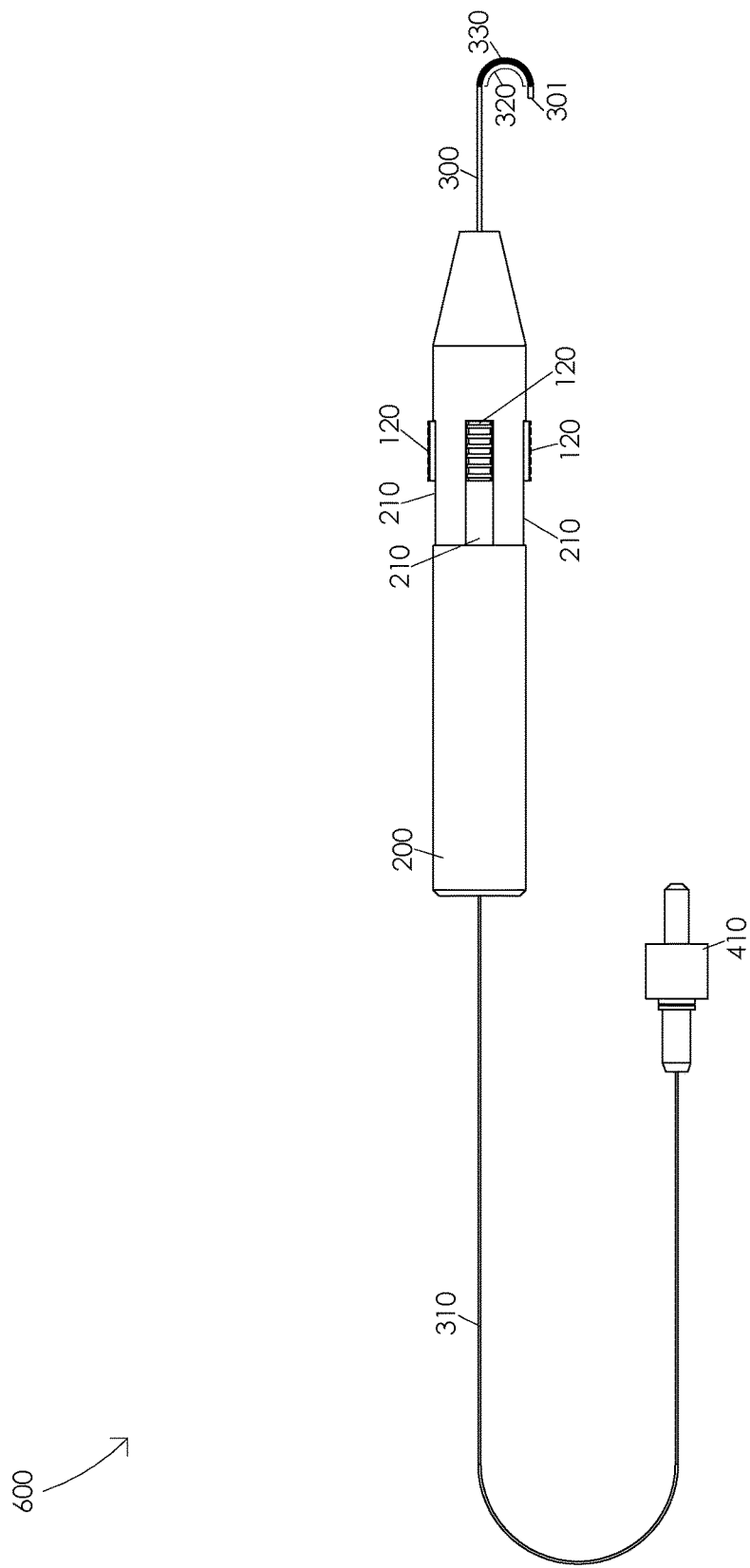
FIGS. 6A, 6B, 6C, 6D, and 6E are schematic diagrams illustrating a gradual straightening of an optic fiber.

FIGS. 6A, 6B, 6C, 6D, and 6E are schematic diagrams illustrating a gradual straightening of an optic fiber 310. FIG. 6A illustrates a fully curved optic fiber 600. In one or more embodiments, optic fiber 310 may comprise a fully curved optic fiber 600, e.g., when housing tube 300 is fully extended relative to handle proximal end 202. Illustratively, optic fiber 310 may comprise a fully curved optic fiber 600, e.g., when an actuation control 120 of a plurality of actuation controls 120 is fully extended relative to an actuation control guide proximal end 212. In one or more embodiments, optic fiber 310 may comprise a fully curved optic fiber 600, e.g., when actuation mechanism 110 is fully extended relative to handle proximal end 202. For example, optic fiber 310 may comprise a fully curved optic fiber 600, e.g., when first housing tube portion 320 is fully compressed. Illustratively, a line tangent to optic fiber distal end 311 may be parallel to a line tangent to housing tube proximal end 302, e.g., when optic fiber 310 comprises a fully curved optic fiber 600.

Figure 6B:
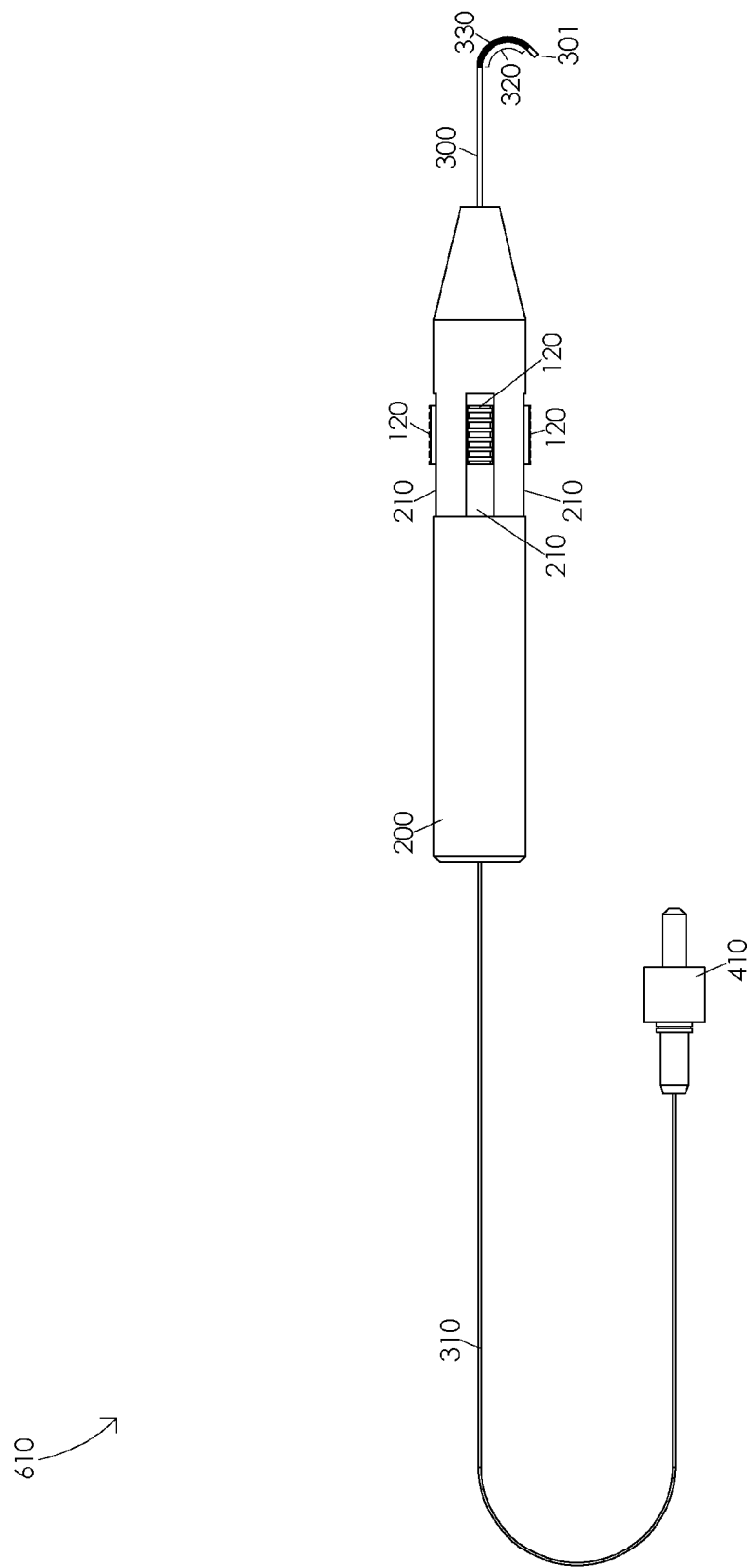

FIG. 6B illustrates an optic fiber in a first partially straightened position 610. In one or more embodiments, an actuation of an actuation control 120 within an actuation control guide 210, e.g., towards actuation control guide proximal end 212 and away from actuation control guide distal end 211, may be configured to gradually straighten optic fiber 310 from a fully curved optic fiber 600 to an optic fiber in a first partially straighten position 610. Illustratively, an actuation of an actuation control 120 within an actuation control guide 210, e.g., towards actuation control guide proximal end 212 and away from actuation control guide distal end 211, may be configured to retract actuation mechanism 110 relative to optic fiber 310. In one or more embodiments, a refraction of actuation mechanism 110 relative to optic fiber 310 may be configured to retract housing tube 300 relative to optic fiber 310. Illustratively, a portion of optic fiber 310, e.g., a portion of optic fiber 310 fixed to a portion of housing tube 300, may be configured to facilitate a refraction of housing tube 300 relative to optic fiber 310. In one or more embodiments, a refraction of housing tube 300 relative to optic fiber 310 may be configured to reduce a force applied to a portion of housing tube 300. Illustratively, a reduction of a force applied to a portion of housing tube 300 may be configured to cause housing tube 300 to gradually straighten, e.g., by decompressing a portion of housing tube 300. For example, a reduction of a force applied to a portion of housing tube 300 may be configured to decompress first housing tube portion 320 causing housing tube 300 to gradually straighten. In one or more embodiments, a gradual straightening of housing tube 300 may be configured to gradually straighten optic fiber 310, e.g., from a fully curved optic fiber 600 to an optic fiber in a first partially straightened position 610. In one or more embodiments, a line tangent to optic fiber distal end 311 may intersect a line tangent to housing tube proximal end 302 at a first partially straightened angle, e.g., when optic fiber 310 comprises an optic fiber in a first partially straightened position 610. Illustratively, the first partially straightened angle may comprise any angle less than 180 degrees. For example, the first partially straightened angle may comprise a 135 degree angle.

Figure 6C:
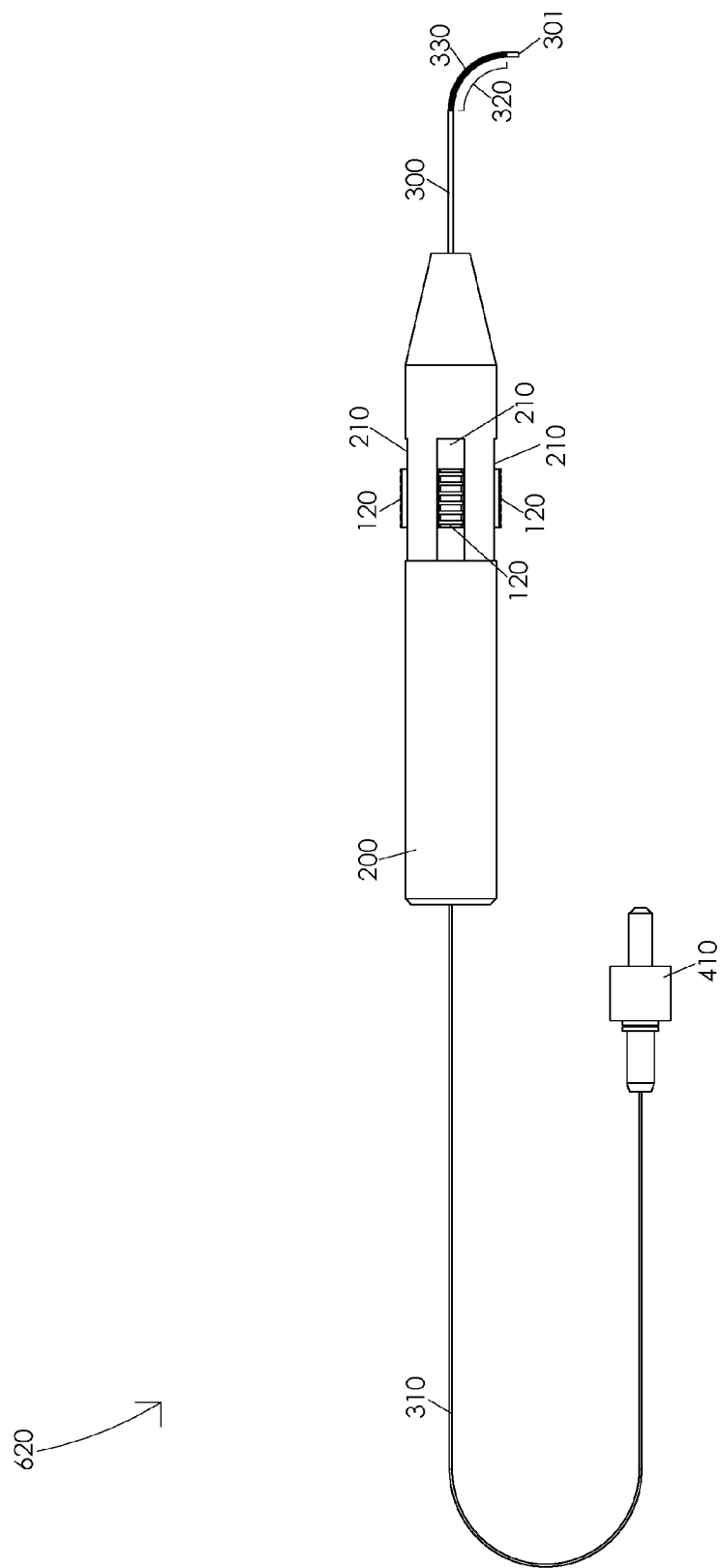

FIG. 6C illustrates an optic fiber in a second partially straightened position 620. In one or more embodiments, an actuation of an actuation control 120 within an actuation control guide 210, e.g., towards actuation control guide proximal end 212 and away from actuation control guide distal end 211, may be configured to gradually straighten optic fiber 310 from an optic fiber in a first partially straighten position 610 to an optic fiber in a second partially straightened position 620. Illustratively, an actuation of an actuation control 120 within an actuation control guide 210, e.g., towards actuation control guide proximal end 212 and away from actuation control guide distal end 211, may be configured to retract actuation mechanism 110 relative to optic fiber 310. In one or more embodiments, a retraction of actuation mechanism 110 relative to optic fiber 310 may be configured to retract housing tube 300 relative to optic fiber 310. Illustratively, a portion of optic fiber 310, e.g., a portion of optic fiber 310 fixed to a portion of housing tube 300, may be configured to facilitate a retraction of housing tube 300 relative to optic fiber 310. In one or more embodiments, a retraction of housing tube 300 relative to optic fiber 310 may be configured to reduce a force applied to a portion of housing tube 300. Illustratively, a reduction of a force applied to a portion of housing tube 300 may be configured to cause housing tube 300 to gradually straighten, e.g., by decompressing a portion of housing tube 300. For example, a reduction of a force applied to a portion of housing tube 300 may be configured to decompress first housing tube portion 320 causing housing tube 300 to gradually straighten. In one or more embodiments, a gradual straightening of housing tube 300 may be configured to gradually straighten optic fiber 310, e.g., from an optic fiber in a first partially straightened position 610 to an optic fiber in a second partially straightened position 620. In one or more embodiments, a line tangent to optic fiber distal end 311 may intersect a line tangent to housing tube proximal end 302 at a second partially straightened angle, e.g., when optic fiber 310 comprises an optic fiber in a second partially straightened position 620. Illustratively, the second partially straightened angle may comprise any angle less than the first partially straightened angle. For example, the second partially straightened angle may comprise a 90 degree angle.

Figure 6D:
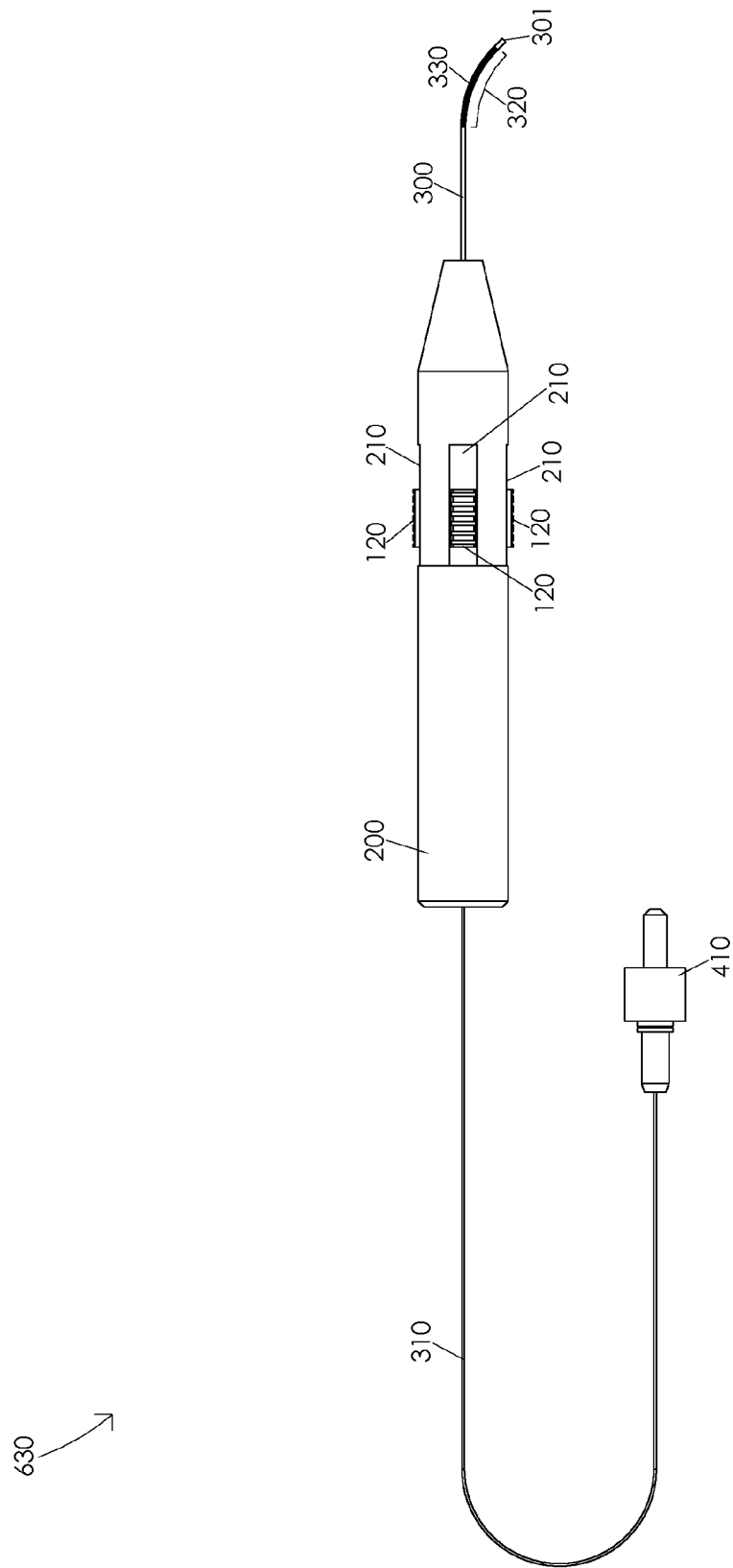

FIG. 6D illustrates an optic fiber in a third partially straightened position 630. In one or more embodiments, an actuation of an actuation control 120 within an actuation control guide 210, e.g., towards actuation control guide proximal end 212 and away from actuation control guide distal end 211, may be configured to gradually straighten optic fiber 310 from an optic fiber in a second partially straightened position 620 to an optic fiber in a third partially straightened position 630. Illustratively, an actuation of an actuation control 120 within an actuation control guide 210, e.g., towards actuation control guide proximal end 212 and away from actuation control guide distal end 211, may be configured to retract actuation mechanism 110 relative to optic fiber 310. In one or more embodiments, a retraction of actuation mechanism 110 relative to optic fiber 310 may be configured to retract housing tube 300 relative to optic fiber 310. Illustratively, a portion of optic fiber 310, e.g., a portion of optic fiber 310 fixed to a portion of housing tube 300, may be configured to facilitate a retraction of housing tube 300 relative to optic fiber 310. In one or more embodiments, a retraction of housing tube 300 relative to optic fiber 310 may be configured to reduce a force applied to a portion of housing tube 300. Illustratively, a reduction of a force applied to a portion of housing tube 300 may be configured to cause housing tube 300 to gradually straighten, e.g., by decompressing a portion of housing tube 300. For example, a reduction of a force applied to a portion of housing tube 300 may be configured to decompress first housing tube portion 320 causing housing tube 300 to gradually straighten. In one or more embodiments, a gradual straightening of housing tube 300 may be configured to gradually straighten optic fiber 310, e.g., from an optic fiber in a second partially straightened position 620 to an optic fiber in a third partially straightened position 630. In one or more embodiments, a line tangent to optic fiber distal end 311 may intersect a line tangent to housing tube proximal end 302 at a third partially straightened angle, e.g., when optic fiber 310 comprises an optic fiber in a third partially straightened position 630. Illustratively, the third partially straightened angle may comprise any angle less than the second partially straightened angle. For example, the third partially straightened angle may comprise a 45 degree angle.

Figure 6E:
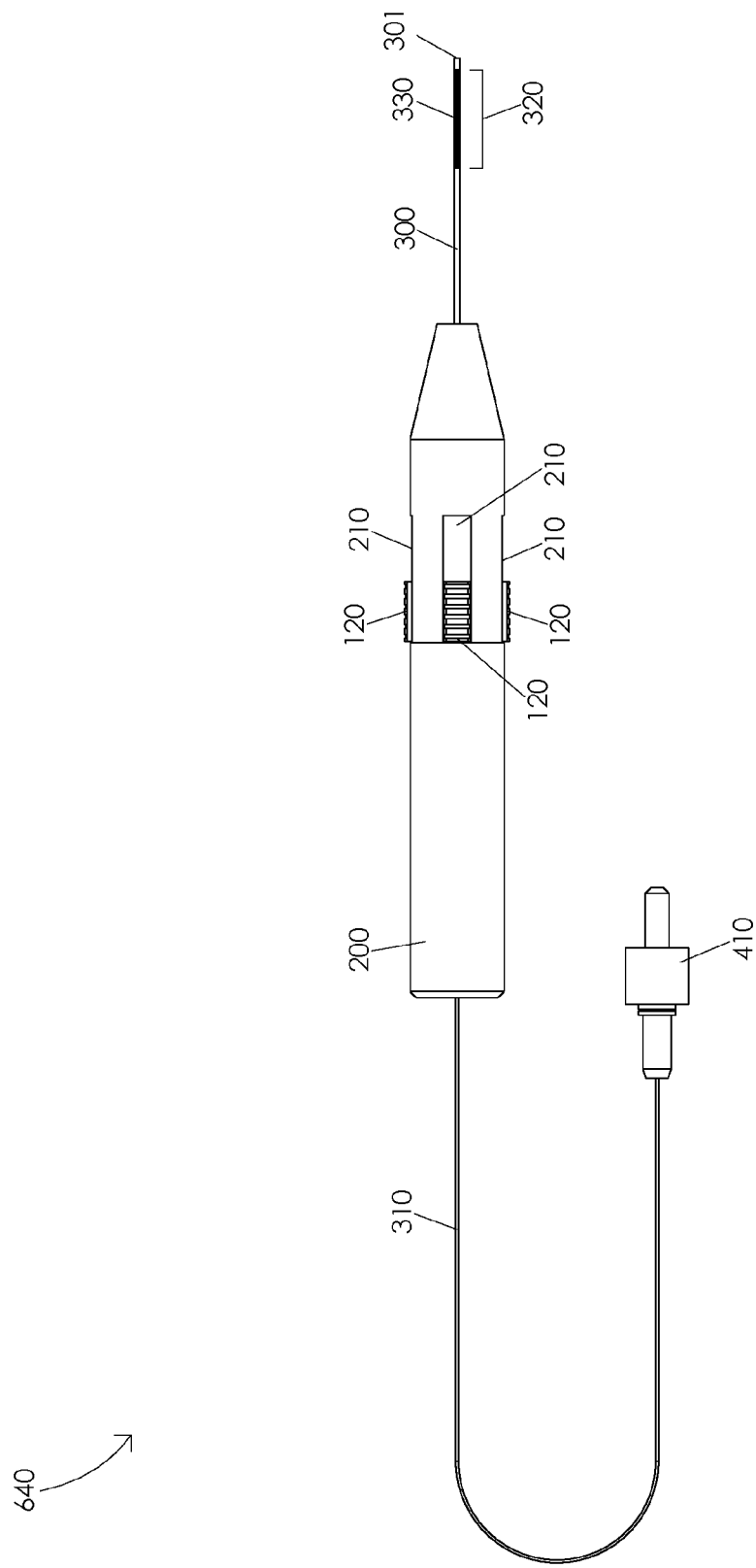

FIG. 6E illustrates an optic fiber in a fully straightened position 640. In one or more embodiments, an actuation of an actuation control 120 within an actuation control guide 210, e.g., towards actuation control guide proximal end 212 and away from actuation control guide distal end 211, may be configured to gradually straighten optic fiber 310 from an optic fiber in a third partially straightened position 630 to an optic fiber in a fully straightened position 640. Illustratively, an actuation of an actuation control 120 within an actuation control guide 210, e.g., towards actuation control guide proximal end 212 and away from actuation control guide distal end 211, may be configured to retract actuation mechanism 110 relative to optic fiber 310. In one or more embodiments, a retraction of actuation mechanism 110 relative to optic fiber 310 may be configured to retract housing tube 300 relative to optic fiber 310. Illustratively, a portion of optic fiber 310, e.g., a portion of optic fiber 310 fixed to a portion of housing tube 300, may be configured to facilitate a retraction of housing tube 300 relative to optic fiber 310. In one or more embodiments, a retraction of housing tube 300 relative to optic fiber 310 may be configured to reduce a force applied to a portion of housing tube 300. Illustratively, a reduction of a force applied to a portion of housing tube 300 may be configured to cause housing tube 300 to gradually straighten, e.g., by decompressing a portion of housing tube 300. For example, a reduction of a force applied to a portion of housing tube 300 may be configured to decompress first housing tube portion 320 causing housing tube 300 to gradually straighten. In one or more embodiments, a gradual straightening of housing tube 300 may be configured to gradually straighten optic fiber 310, e.g., from an optic fiber in a third partially straightened position 630 to an optic fiber in a fully straightened position 640. In one or more embodiments, a line tangent to optic fiber distal end 311 may be parallel to a line tangent to housing tube proximal end 302, e.g., when optic fiber 310 comprises an optic fiber in a fully straightened position 640.

Illustratively, a surgeon may aim optic fiber distal end 311 at any of a plurality of targets within an eye, e.g., to perform a photocoagulation procedure, to illuminate a surgical target site, etc. In one or more embodiments, a surgeon may aim optic fiber distal end 311 at any target within a particular transverse plane of the inner eye by, e.g., rotating handle 200 to orient housing tube 300 in an orientation configured to cause a curvature of housing tube 300 within the particular transverse plane of the inner eye and varying an amount of actuation of an actuation control 120 of a plurality of actuation controls 120. Illustratively, a surgeon may aim optic fiber distal end 311 at any target within a particular sagittal plane of the inner eye by, e.g., rotating handle 200 to orient housing tube 300 in an orientation configured to cause a curvature of housing tube 300 within the particular sagittal plane of the inner eye and varying an amount of actuation of an actuation control 120 of a plurality of actuation controls 120. In one or more embodiments, a surgeon may aim optic fiber distal end 311 at any target within a particular frontal plane of the inner eye by, e.g., varying an amount of actuation of an actuation control 120 of a plurality of actuation controls 120 to orient a line tangent to optic fiber distal end 311 wherein the line tangent to optic fiber distal end 311 is within the particular frontal plane of the inner eye and rotating handle 200. Illustratively, a surgeon may aim optic fiber distal end 311 at any target located outside of the particular transverse plane, the particular sagittal plane, and the particular frontal plane of the inner eye, e.g., by varying a rotational orientation of handle 200 and varying an amount of actuation of an actuation control 120 of a plurality of actuation controls 120. In one or more embodiments, a surgeon may aim optic fiber distal end 311 at any target of a plurality of targets within an eye, e.g., without increasing a length of a portion of a steerable laser probe within the eye. Illustratively, a surgeon may aim optic fiber distal end 311 at any target of a plurality of targets within an eye, e.g., without decreasing a length of a portion of a steerable laser probe within the eye.

FIGS. 7A and 7B are schematic diagrams illustrating an exploded view of a handle assembly 700. FIG. 7A illustrates a side view of handle assembly 700. In one or more embodiments, handle assembly 700 may comprise a handle end cap 705 having a handle end cap distal end 706 and a handle end cap proximal end 707, an actuation mechanism 710 having an actuation mechanism distal end 711 and an actuation mechanism proximal end 712, and a handle base 730 having a handle base distal end 731 and a handle base proximal end 732. Illustratively, actuation mechanism 710 may comprise a plurality of actuation controls 720. For example, each actuation control 720 of a plurality of actuation controls 720 may comprise an actuation control distal end 721 and an actuation control proximal end 722. In one or more embodiments, handle base 730 may comprise a plurality of handle base limbs 733, a plurality of handle base channels 734, and a handle end cap interface 735.

FIG. 7B illustrates a cross-sectional view of handle assembly 700. In one or more embodiments, handle assembly 700 may comprise a proximal chamber 740, a handle base housing 750, a handle base interface 755, a cable housing 760, an inner bore 770, a housing tube housing 775, an actuation mechanism guide 780, a pressure mechanism housing 785, and a housing tube guide 790. Handle end cap 705, actuation mechanism 710, actuation control 720, and handle base 730 may be manufactured from any suitable material, e.g., polymers, metals, metal alloys, etc., or from any combination of suitable materials.

FIGS. 8A and 8B are schematic diagrams illustrating a handle 800. FIG. 8A illustrates a side view of handle 800. In one or more embodiments, handle 800 may comprise a handle distal end 801, a handle proximal end 802, and a plurality of actuation control guides 810. For example, each actuation control guide 810 of a plurality of actuation control guides 810 may comprise an actuation control guide distal end 811 and an actuation control guide proximal end 812. Illustratively, handle distal end 801 may comprise handle base distal end 731. In one or more embodiments, handle proximal end 802 may comprise handle end cap proximal end 707.

FIG. 8B illustrates a cross-sectional view of handle 800. Illustratively, actuation mechanism 710 may be disposed within handle end cap 705 and handle base 730. In one or more embodiments, a portion of actuation mechanism 710 may be disposed within handle base housing 750, e.g., actuation mechanism proximal end 712 may be disposed within handle base housing 750. Illustratively, a portion of actuation mechanism 710 may be disposed within actuation mechanism guide 780, e.g., actuation mechanism distal end 711 may be disposed within actuation mechanism guide 780. In one or more embodiments, a portion of handle base 730 may be disposed within handle end cap 705, e.g., handle base proximal end 732 may be disposed within handle end cap 705. Illustratively, a portion of handle base 730 may be disposed within handle base housing 750. In one or more embodiments, a portion of handle base 730 may be disposed within handle base housing 750, e.g., handle base proximal end 732 may be configured to interface with handle base interface 755. Illustratively, a portion of handle base 730 may be disposed within handle base housing 750, e.g., handle end cap distal end 706 may be configured to interface with handle end cap interface 735. In one or more embodiments, a portion of handle base 730 may be fixed within a portion of handle end cap 705, e.g., by an adhesive or any suitable fixation means. For example, a portion of handle base 730 may be fixed within handle base housing 750, e.g., by an adhesive or any suitable fixation means.

Illustratively, each actuation control 720 of a plurality of actuation controls 720 may be disposed within an actuation control guide 810 of a plurality of actuation control guides 810. In one or more embodiments, each actuation control guide 810 of a plurality of actuation control guides 810 may comprise a handle base channel 734 of a plurality of handle base channels 734. In one or more embodiments, at least one actuation control 720 may be configured to actuate within at least one actuation control guide 810. Illustratively, each actuation control 720 of a plurality of actuation controls 720 may be configured to actuate within an actuation control guide 810 of a plurality of actuation control guides 810. In one or more embodiments, an actuation of a particular actuation control 720 in a particular actuation control guide 810 may be configured to actuate each actuation control 720 of a plurality of actuation controls 720. In one or more embodiments, actuation controls 720 may be configured to actuate within actuation control guides 810 in pairs or groups. Illustratively, an actuation of first actuation control 720 within a first actuation control guide 810 may be configured to actuate a second actuation control 720 within a second actuation control guide 810.

In one or more embodiments, actuation mechanism 710 may be configured to actuate within actuation mechanism guide 780. For example, actuation mechanism guide 780 may comprise a lubricant configured to facilitate an actuation of actuation mechanism 710 within actuation mechanism guide 780. Illustratively, an actuation of an actuation control 720 within an actuation control guide 810 may be configured to actuate actuation mechanism 710, e.g., within actuation mechanism guide 780. In one or more embodiments, an actuation of an actuation control 720 towards an actuation control guide distal end 811, e.g., and away from an actuation control guide proximal end 812, may be configured to actuate actuation mechanism 710 towards handle distal end 801, e.g., and away from handle proximal end 802. Illustratively, an actuation of an actuation control 720 towards an actuation control guide proximal end 812, e.g., and away from an actuation control guide distal end 811, may be configured to actuate actuation mechanism towards handle proximal end 802, e.g., and away from handle distal end 801.

In one or more embodiments, a surgeon may actuate actuation mechanism 710 within actuation mechanism guide 780, e.g., by manipulating an actuation control 720 of a plurality of actuation controls 720 when handle 800 is in a first rotational orientation. Illustratively, the surgeon may rotate handle 800 and actuate actuation mechanism 710 within actuation mechanism guide 780, e.g., by manipulating an actuation control 720 of a plurality of actuation controls 720 when handle 800 is in a second rotational orientation. In one or more embodiments, the surgeon may rotate handle 800 and actuate actuation mechanism 710 within actuation mechanism guide 780, e.g., by manipulating an actuation control 720 of a plurality of actuation controls 720 when handle 800 is in a third rotational orientation. Illustratively, a surgeon may actuate actuation mechanism 710 within actuation mechanism guide 780, e.g., by manipulating an actuation control 720 of a plurality of actuation controls 720 when handle 800 is in any rotational orientation of a plurality of rotational orientations.

Figure 9:
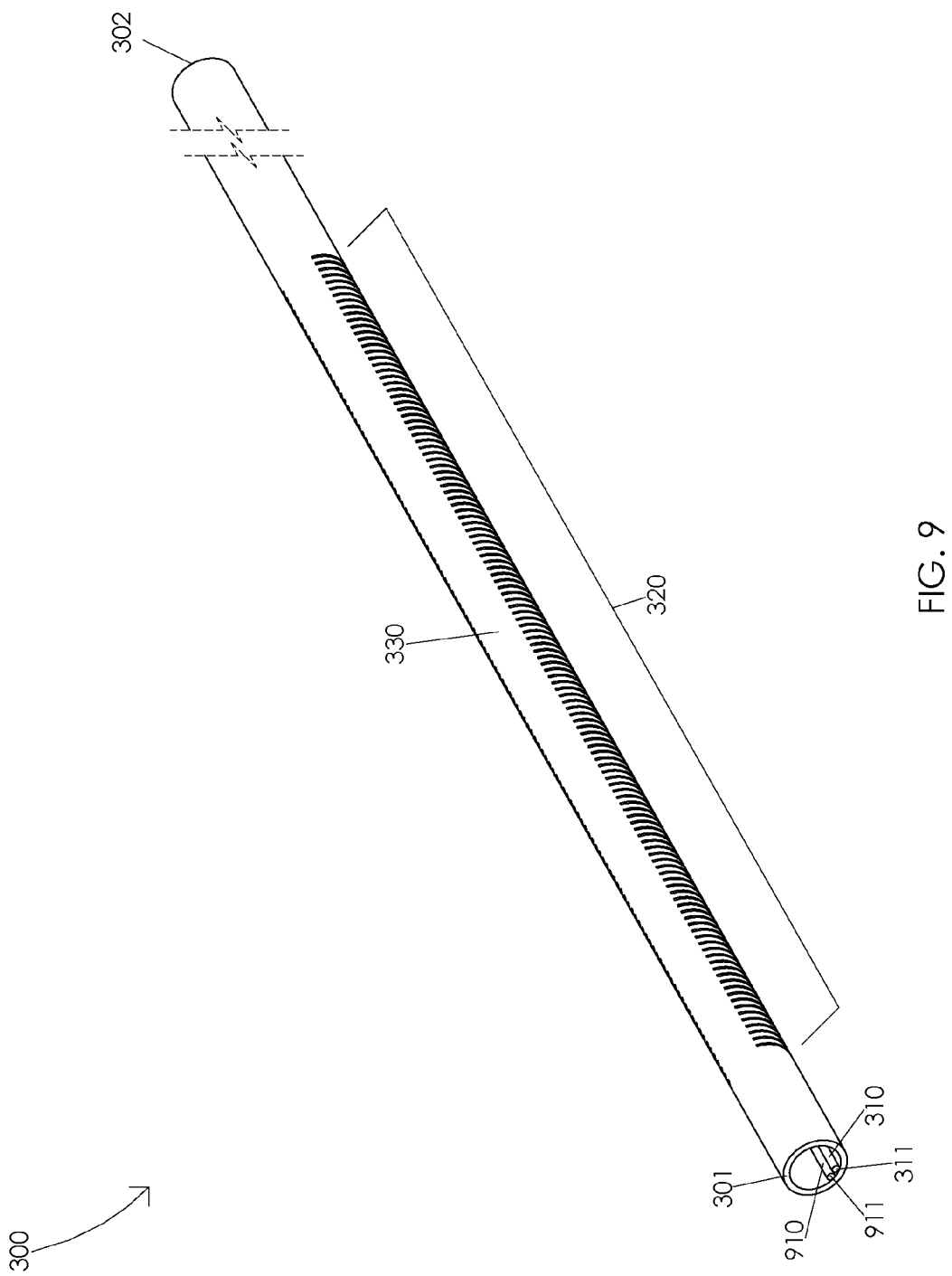
FIG. 9 is a schematic diagram illustrating a housing tube.

FIG. 9 illustrates an angled view of housing tube 300. Illustratively, an optic fiber 310 may be disposed within housing tube 300. In one or more embodiments, optic fiber 310 may comprise an optic fiber distal end 311 and an optic fiber proximal end 312. Illustratively, optic fiber 310 may be configured to transmit light, e.g., laser light, illumination light, etc. In one or more embodiments, optic fiber 310 may be disposed within housing tube 300 wherein optic fiber distal end 311 is adjacent to housing tube distal end 301.

Illustratively, optic fiber 310 may be disposed within housing tube 300 wherein a portion of optic fiber 310 may be adjacent to a portion of first housing tube portion 320. In one or more embodiments, a portion of optic fiber 310 may be fixed to an inner portion of housing tube 300, e.g., by an adhesive or any suitable fixation means.

Illustratively, a cable 910 may be disposed within housing tube 300. In one or more embodiments, cable 910 may comprise a cable distal end 911 and a cable proximal end 912. Illustratively, cable 910 may be manufactured from any suitable material, e.g., polymers, metals, metal alloys, etc., or from any combination of suitable materials. In one or more embodiments, cable 910 may be disposed within housing tube 300 wherein cable distal end 911 is adjacent to housing tube distal end 301. Illustratively, cable 910 may be disposed within housing tube 300 wherein a portion of cable 910 may be adjacent to a portion of first housing tube portion 320.

Figure 10:
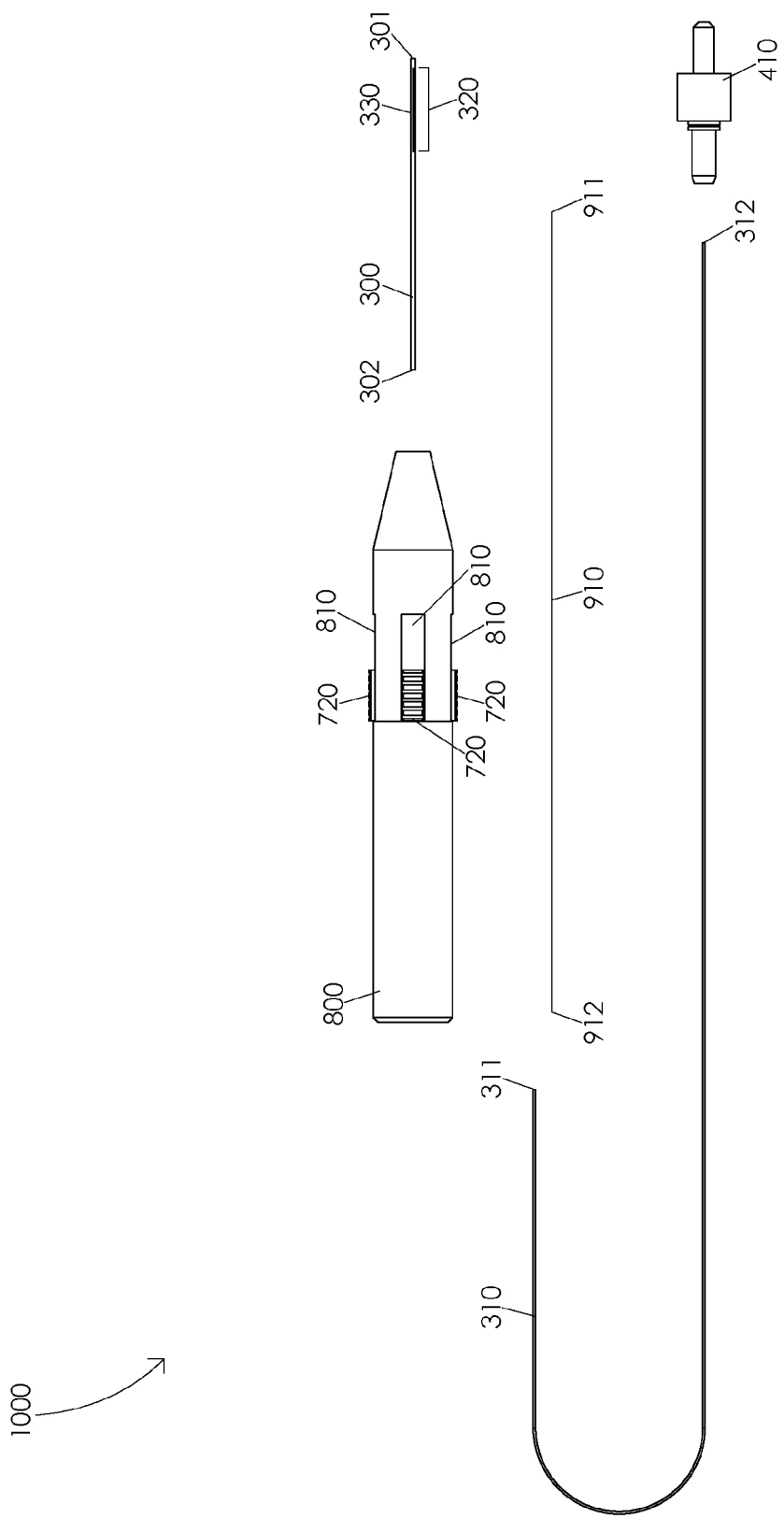
FIG. 10 is a schematic diagram illustrating an exploded view of a steerable laser probe assembly.

FIG. 10 is a schematic diagram illustrating an exploded view of a steerable laser probe assembly 1000. In one or more embodiments, steerable laser probe assembly 1000 may comprise a handle 800, a housing tube 300 having a housing tube distal end 301 and a housing tube proximal end 302, an optic fiber 310 having an optic fiber distal end 311 and an optic fiber proximal end 312, a cable 910 having a cable distal end 911 and a cable proximal end 912, and a light source interface 410. Illustratively, light source interface 410 may be configured to interface with optic fiber 310, e.g., at optic fiber proximal end 312. In one or more embodiments, light source interface 410 may comprise a standard light source connecter, e.g., an SMA connector.

Illustratively, a portion of housing tube 300 may be fixed to actuation mechanism 710, e.g., housing tube proximal end 302 may be fixed to actuation mechanism distal end 711. In one or more embodiments, a portion of housing tube 300 may be fixed to actuation mechanism 710, e.g., by an adhesive or any suitable fixation means. Illustratively, a portion of housing tube 300 may be disposed within actuation mechanism 710, e.g., housing tube proximal end 302 may be disposed within housing tube housing 775. In one or more embodiments, a portion of housing tube 300 may be fixed within housing tube housing 775, e.g., by an adhesive or any suitable fixation means. Illustratively, housing tube 300 may be disposed within actuation mechanism guide 780 and housing tube guide 790. In one or more embodiments, a portion of housing tube 300 may extend from handle distal end 801, e.g., housing tube distal end 301 may extend from handle distal end 801.

Illustratively, optic fiber 310 may be disposed within cable housing 760, proximal chamber 740, inner bore 770, housing tube housing 775, housing tube 300, actuation mechanism guide 780, and housing tube guide 990. In one or more embodiments, a portion of optic fiber 310 may be fixed to a portion of housing tube 300, e.g., by an adhesive or any suitable fixation means. Illustratively, cable 910 may be disposed within cable housing 760, proximal chamber 740, inner bore 770, housing tube housing 775, housing tube 300, actuation mechanism guide 780, and housing tube guide 990. In one or more embodiments, a portion of cable 910 may be fixed to a portion of housing tube 300, e.g., by an adhesive or any suitable fixation means. Illustratively, a portion of cable 910 may be fixed in a position relative to handle 800. In one or more embodiments, a portion of cable 910 may be fixed within cable housing 760, e.g., by an adhesive or any suitable fixation means. Illustratively, a portion of cable 910 may be fixed within cable housing 760, e.g., by a press fit or any suitable fixation means. In one or more embodiments, a portion of cable 910 may be fixed to a portion of housing tube 300 and a portion of cable 910 may be fixed in a position relative to handle 800.

Illustratively, an actuation of an actuation control 720 within an actuation control guide 810, e.g., towards actuation control guide distal end 811 and away from actuation control guide proximal end 812, may be configured to actuate actuation mechanism 710 within actuation mechanism guide 780, e.g., towards handle distal end 801 and away from handle proximal end 802. In one or more embodiments, an actuation of actuation mechanism 710 towards handle distal end 801 and away from handle proximal end 802 may be configured to extend actuation mechanism 710 relative to cable 910. Illustratively, an extension of actuation mechanism 710 relative to cable 910 may be configured to extend housing tube 300 relative to cable 910. In one or more embodiments, cable 910 may be configured to resist an extension of housing tube 300 relative to cable 910. Illustratively, cable 910 may be configured to resist an extension of housing tube 300 relative to cable 910, e.g., a portion of cable 910 may be configured to apply a force to a portion of housing tube 300. In one or more embodiments, an application of a force, e.g., a resistive force, to a portion of housing tube 300 may be configured to compress a portion of housing tube 300 causing housing tube 300 to gradually curve. For example, an application of a force to a portion of housing tube 300 may be configured to compress first housing tube portion 320 causing housing tube 300 to gradually curve. Illustratively, a gradual curving of housing tube 300 may be configured to gradually curve optic fiber 310. In one or more embodiments, an actuation of an actuation control 720 within an actuation control guide 810, e.g., towards actuation control guide distal end 811 and away from actuation control guide proximal end 812, may be configured to gradually curve optic fiber 310.

Illustratively, an actuation of an actuation control 720 within an actuation control guide 810, e.g., towards actuation control guide proximal end 812 and away from actuation control guide distal end 811, may be configured to actuate actuation mechanism 710 within actuation mechanism guide 780, e.g., towards handle proximal end 802 and away from handle distal end 801. In one or more embodiments, an actuation of actuation mechanism 710 towards handle proximal end 802 and away from handle distal end 801 may be configured to retract actuation mechanism 710 relative to cable 910. Illustratively, a retraction of actuation mechanism 710 relative to cable 910 may be configured to retract housing tube 300 relative to cable 910. In one or more embodiments, cable 910 may be configured to facilitate a retraction of housing tube 300 relative to cable 910. Illustratively, cable 910 may be configured to facilitate a retraction of housing tube 300 relative to cable 910, e.g., a portion of cable 910 may be configured to reduce a force applied to a portion of housing tube 300. In one or more embodiments, a reduction of a force, e.g., a resistive force, applied to a portion of housing tube 300 may be configured to decompress a portion of housing tube 300 causing housing tube 300 to gradually straighten. For example, a reduction of a force applied to a portion of housing tube 300 may be configured to decompress first housing tube portion 320 causing housing tube 300 to gradually straighten. Illustratively, a gradual straightening of housing tube 300 may be configured to gradually straighten optic fiber 310. In one or more embodiments, an actuation of an actuation control 720 within an actuation control guide 810, e.g., towards actuation control guide proximal end 812 and away from actuation control guide distal end 811, may be configured to gradually straighten optic fiber 310.

Figure 11A:
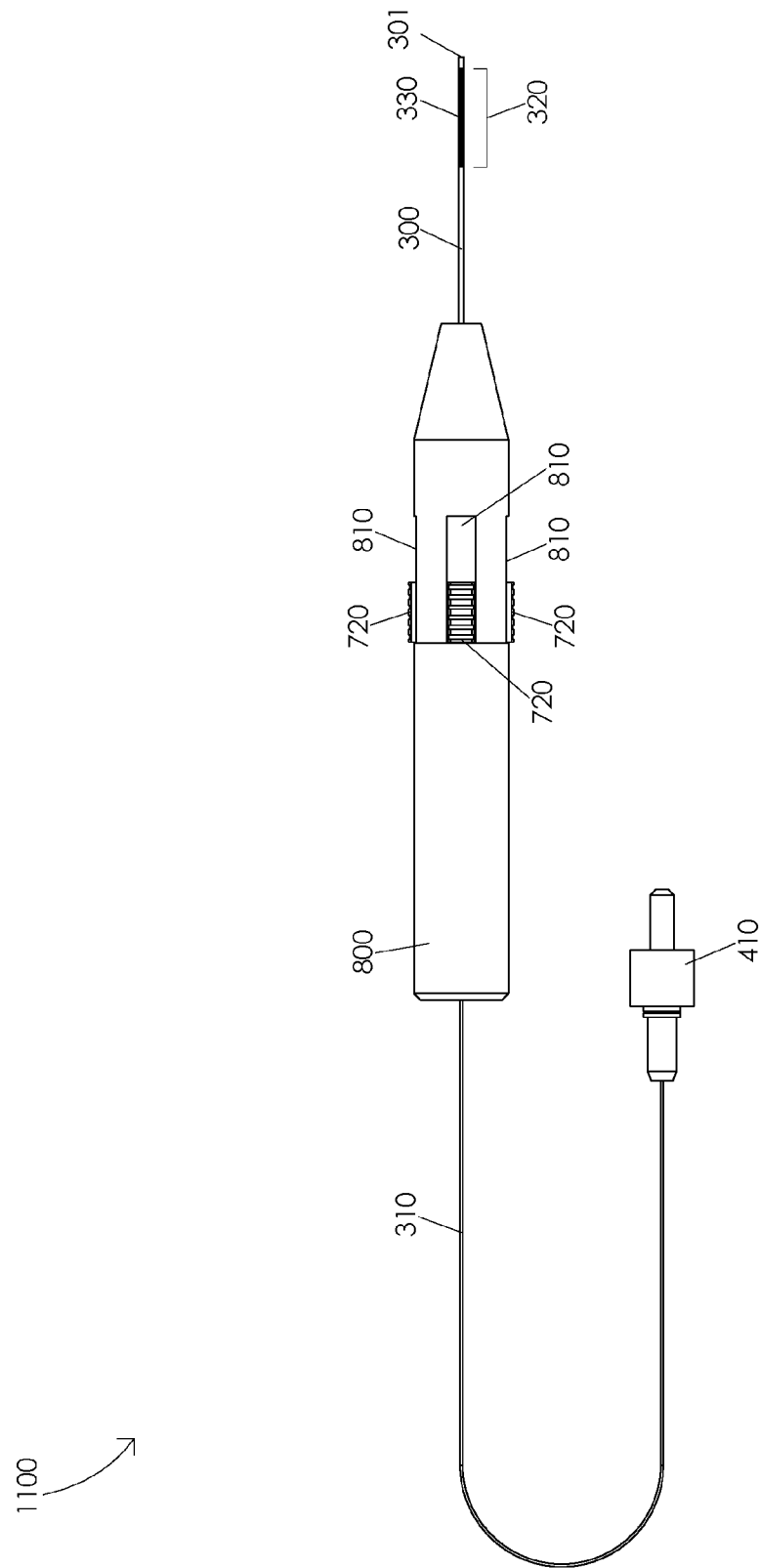
FIGS. 11A, 11B, 11C, 11D, and 11E are schematic diagrams illustrating a gradual curving of an optic fiber.

FIGS. 11A, 11B, 11C, 11D, and 11E are schematic diagrams illustrating a gradual curving of an optic fiber 310. FIG. 11A illustrates a straight optic fiber 1100. In one or more embodiments, optic fiber 310 may comprise a straight optic fiber 1100, e.g., when housing tube 300 is fully retracted relative to handle proximal end 802. Illustratively, optic fiber 310 may comprise a straight optic fiber 1100, e.g., when an actuation control 720 of a plurality of actuation controls 720 is fully retracted relative to an actuation control guide proximal end 812. In one or more embodiments, optic fiber 310 may comprise a straight optic fiber 1100, e.g., when actuation mechanism 710 is fully retracted relative to handle proximal end 802. For example, optic fiber 310 may comprise a straight optic fiber 1100, e.g., when first housing tube portion 320 is fully decompressed. Illustratively, a line tangent to optic fiber distal end 311 may be parallel to a line tangent to housing tube proximal end 302, e.g., when optic fiber 310 comprises a straight optic fiber 1100.

Figure 11B:
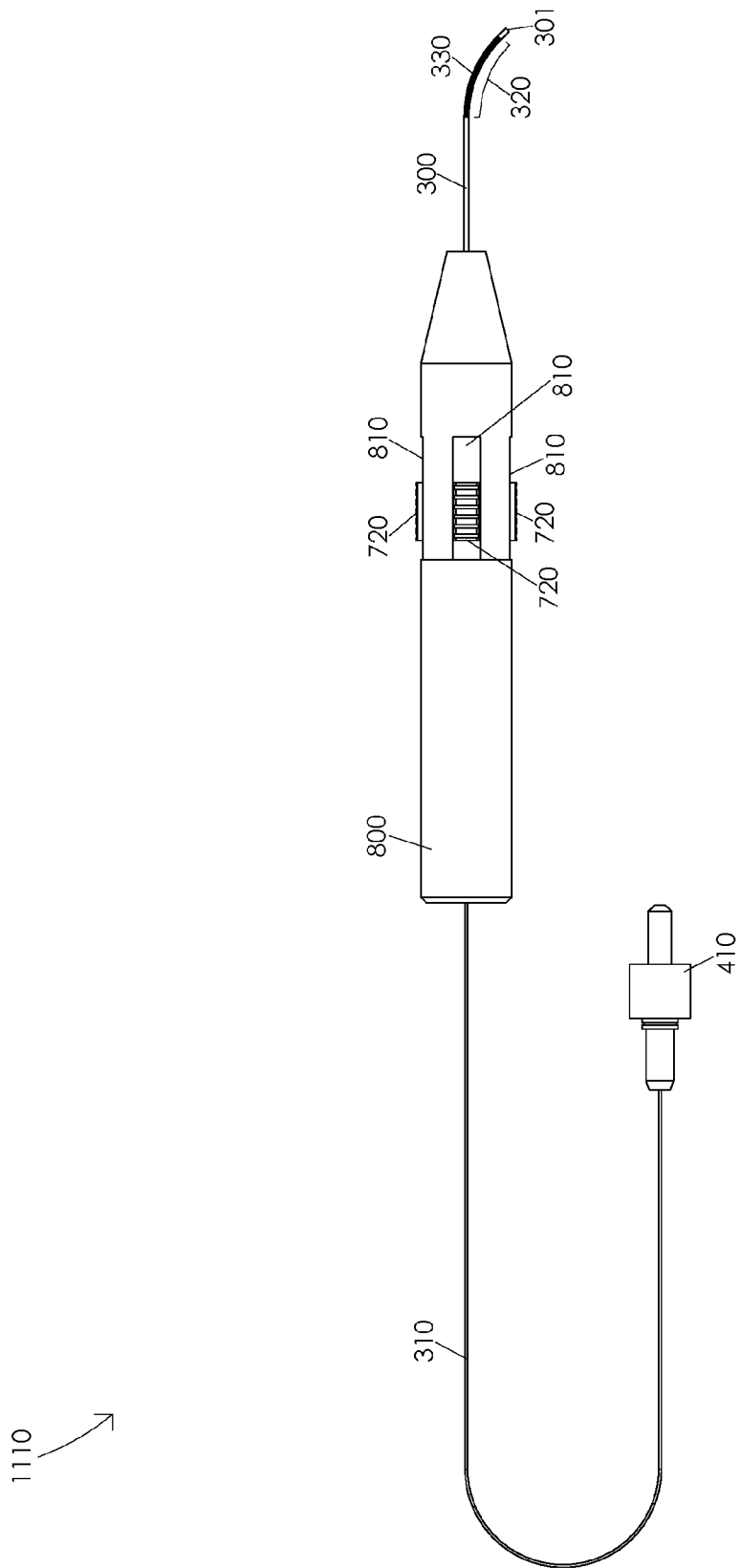

FIG. 11B illustrates an optic fiber in a first curved position 1110. In one or more embodiments, an actuation of an actuation control 720 within an actuation control guide 810, e.g., towards actuation control guide distal end 811 and away from actuation control guide proximal end 812, may be configured to gradually curve optic fiber 310 from a straight optic fiber 1100 to an optic fiber in a first curved position 1110. Illustratively, an actuation of an actuation control 720 within an actuation control guide 810, e.g., towards actuation control guide distal end 811 and away from actuation control guide proximal end 812, may be configured to extend actuation mechanism 710 relative to cable 910. In one or more embodiments, an extension of actuation mechanism 710 relative to cable 910 may be configured to extend housing tube 300 relative to cable 910. Illustratively, a portion of cable 910, e.g., a portion of cable 910 fixed to a portion of housing tube 300, may be configured to resist an extension of housing tube 300 relative to cable 910. In one or more embodiments, an extension of housing tube 300 relative to cable 910 may be configured to apply a force to a portion of housing tube 300. Illustratively, an application of a force to a portion of housing tube 300 may be configured to cause housing tube 300 to gradually curve, e.g., by compressing a portion of housing tube 300. For example, an application of a force to a portion of housing tube 300 may be configured to compress first housing tube portion 320 causing housing tube 300 to gradually curve. In one or more embodiments, a gradual curving of housing tube 300 may be configured to gradually curve optic fiber 310, e.g., from a straight optic fiber 1100 to an optic fiber in a first curved position 1110. In one or more embodiments, a line tangent to optic fiber distal end 311 may intersect a line tangent to housing tube proximal end 302 at a first angle, e.g., when optic fiber 310 comprises an optic fiber in a first curved position 1110. Illustratively, the first angle may comprise any angle greater than zero degrees. For example, the first angle may comprise a 45 degree angle.

Figure 11C:
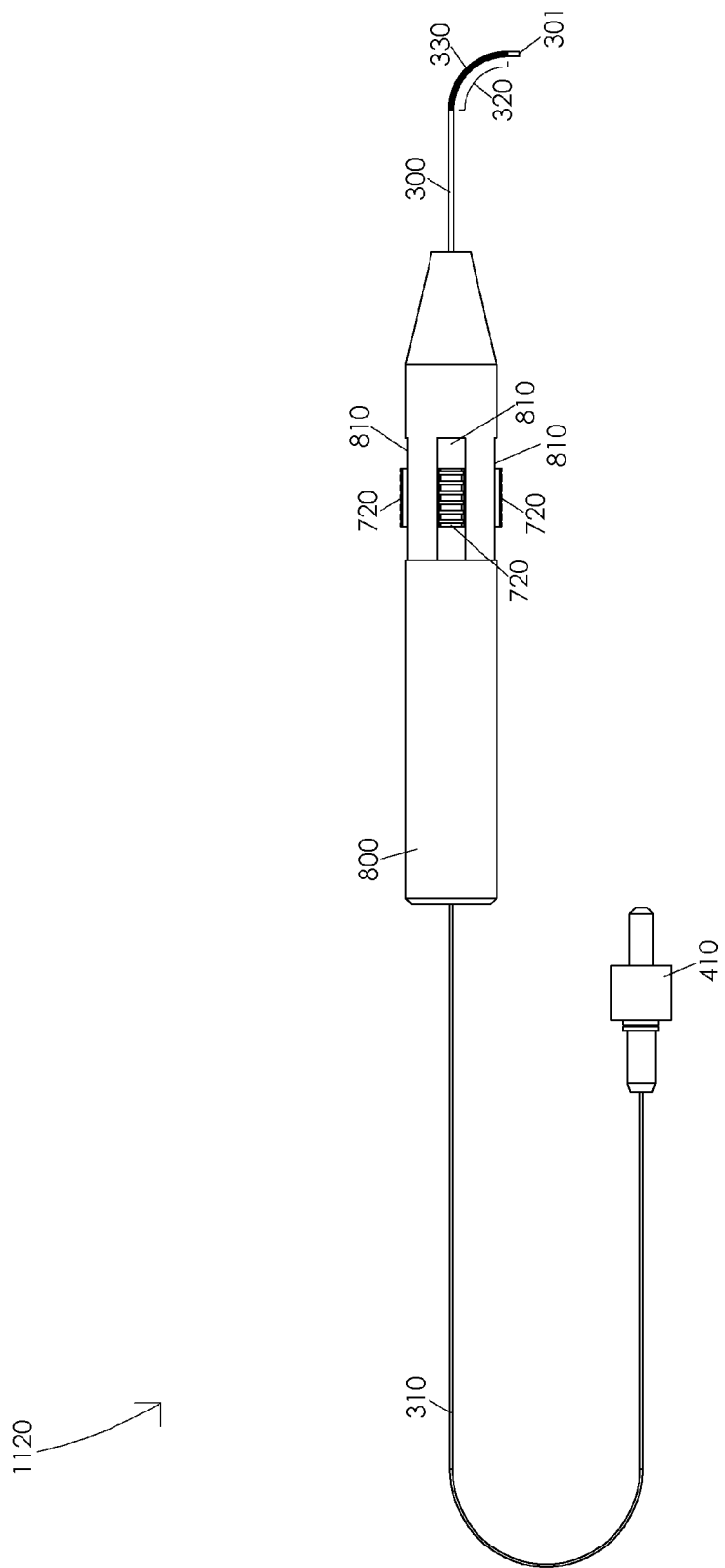

FIG. 11C illustrates an optic fiber in a second curved position 1120. In one or more embodiments, an actuation of an actuation control 720 within an actuation control guide 810, e.g., towards actuation control guide distal end 811 and away from actuation control guide proximal end 812, may be configured to gradually curve optic fiber 310 from an optic fiber in a first curved position 1110 to an optic fiber in a second curved position 1120. Illustratively, an actuation of an actuation control 720 within an actuation control guide 810, e.g., towards actuation control guide distal end 811 and away from actuation control guide proximal end 812, may be configured to extend actuation mechanism 710 relative to cable 910. In one or more embodiments, an extension of actuation mechanism 710 relative to cable 910 may be configured to extend housing tube 300 relative to cable 910. Illustratively, a portion of cable 910, e.g., a portion of cable 910 fixed to a portion of housing tube 300, may be configured to resist an extension of housing tube 300 relative to cable 910. In one or more embodiments, an extension of housing tube 300 relative to cable 910 may be configured to apply a force to a portion of housing tube 300. Illustratively, an application of a force to a portion of housing tube 300 may be configured to cause housing tube 300 to gradually curve, e.g., by compressing a portion of housing tube 300. For example, an application of a force to a portion of housing tube 300 may be configured to compress first housing tube portion 320 causing housing tube 300 to gradually curve. In one or more embodiments, a gradual curving of housing tube 300 may be configured to gradually curve optic fiber 310, e.g., from an optic fiber in a first curved position 1110 to an optic fiber in a second curved position 1120. In one or more embodiments, a line tangent to optic fiber distal end 311 may intersect a line tangent to housing tube proximal end 302 at a second angle, e.g., when optic fiber 310 comprises an optic fiber in a second curved position 1120. Illustratively, the second angle may comprise any angle greater than the first angle. For example, the second angle may comprise a 90 degree angle.

Figure 11D:
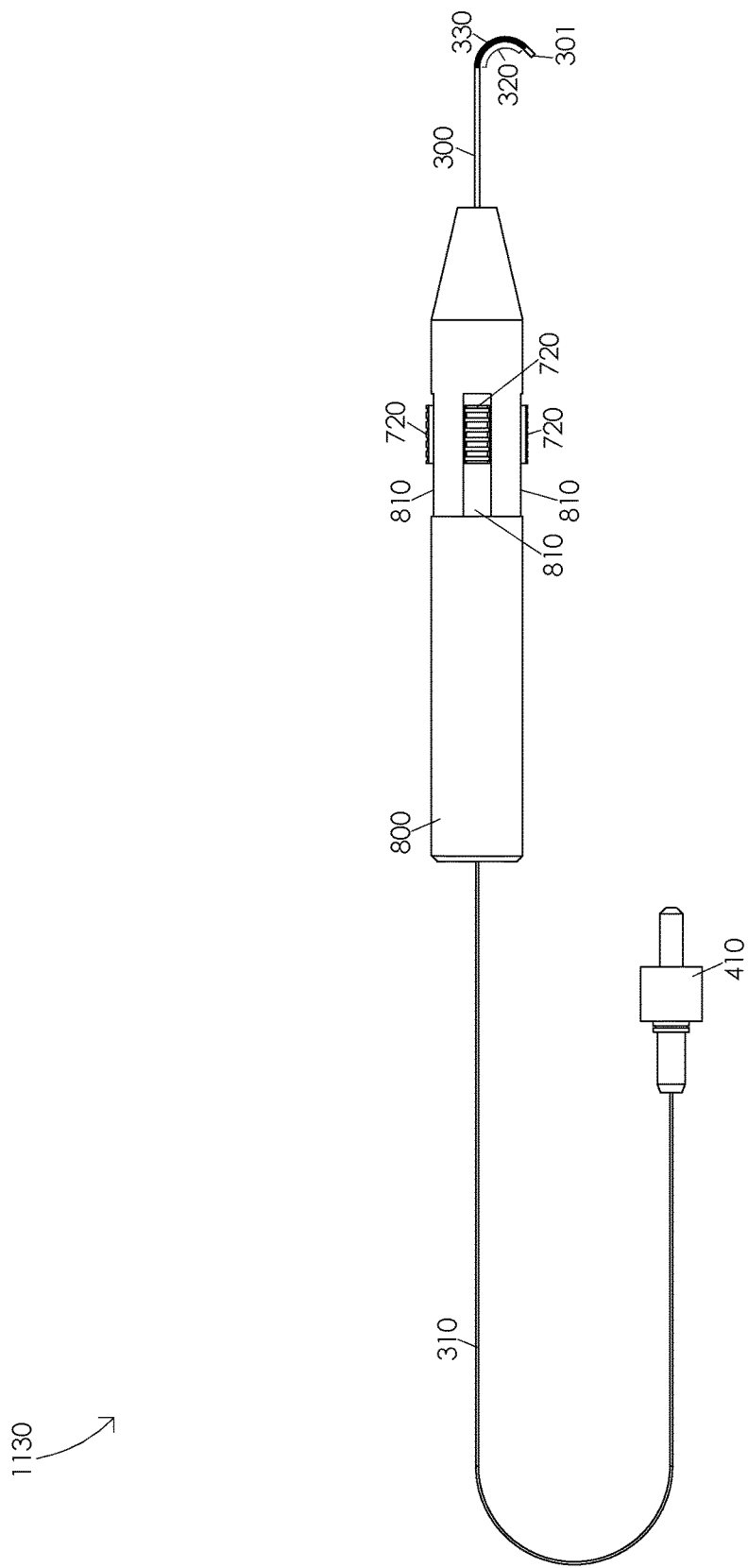

FIG. 11D illustrates an optic fiber in a third curved position 1130. In one or more embodiments, an actuation of an actuation control 720 within an actuation control guide 810, e.g., towards actuation control guide distal end 811 and away from actuation control guide proximal end 812, may be configured to gradually curve optic fiber 310 from an optic fiber in a second curved position 1120 to an optic fiber in a third curved position 1130. Illustratively, an actuation of an actuation control 720 within an actuation control guide 810, e.g., towards actuation control guide distal end 811 and away from actuation control guide proximal end 812, may be configured to extend actuation mechanism 710 relative to cable 910. In one or more embodiments, an extension of actuation mechanism 710 relative to cable 910 may be configured to extend housing tube 300 relative to cable 910. Illustratively, a portion of cable 910, e.g., a portion of cable 910 fixed to a portion of housing tube 300, may be configured to resist an extension of housing tube 300 relative to cable 910. In one or more embodiments, an extension of housing tube 300 relative to cable 910 may be configured to apply a force to a portion of housing tube 300. Illustratively, an application of a force to a portion of housing tube 300 may be configured to cause housing tube 300 to gradually curve, e.g., by compressing a portion of housing tube 300. For example, an application of a force to a portion of housing tube 300 may be configured to compress first housing tube portion 320 causing housing tube 300 to gradually curve. In one or more embodiments, a gradual curving of housing tube 300 may be configured to gradually curve optic fiber 310, e.g., from an optic fiber in a second curved position 1120 to an optic fiber in a third curved position 1130. In one or more embodiments, a line tangent to optic fiber distal end 311 may intersect a line tangent to housing tube proximal end 302 at a third angle, e.g., when optic fiber 310 comprises an optic fiber in a third curved position 1130. Illustratively, the third angle may comprise any angle greater than the second angle. For example, the third angle may comprise a 135 degree angle.

Figure 11E:
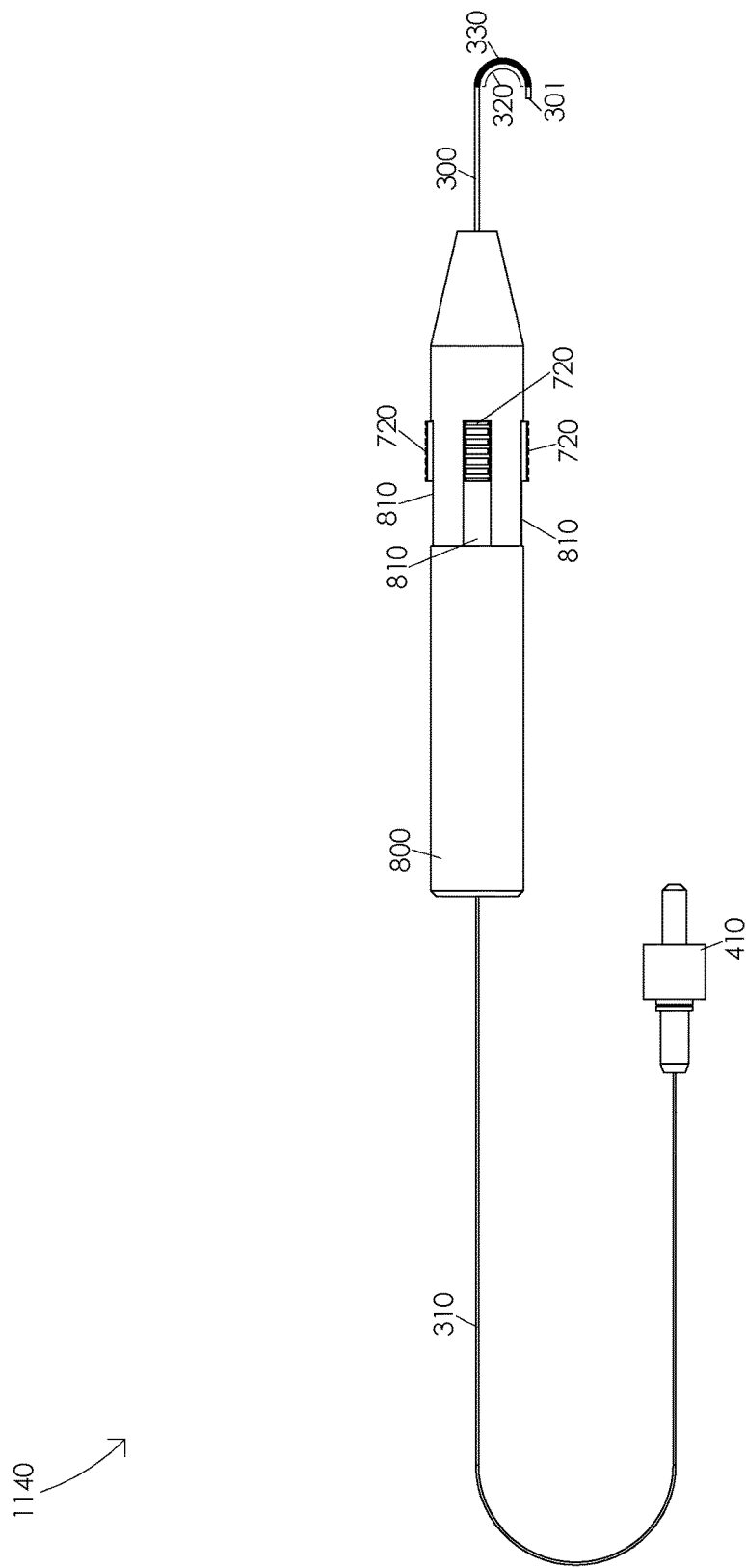

FIG. 11E illustrates an optic fiber in a fourth curved position 1140. In one or more embodiments, an actuation of an actuation control 720 within an actuation control guide 810, e.g., towards actuation control guide distal end 811 and away from actuation control guide proximal end 812, may be configured to gradually curve optic fiber 310 from an optic fiber in a third curved position 1130 to an optic fiber in a fourth curved position 1140. Illustratively, an actuation of an actuation control 720 within an actuation control guide 810, e.g., towards actuation control guide distal end 811 and away from actuation control guide proximal end 812, may be configured to extend actuation mechanism 710 relative to cable 910. In one or more embodiments, an extension of actuation mechanism 710 relative to cable 910 may be configured to extend housing tube 300 relative to cable 910. Illustratively, a portion of cable 910, e.g., a portion of cable 910 fixed to a portion of housing tube 300, may be configured to resist an extension of housing tube 300 relative to cable 910. In one or more embodiments, an extension of housing tube 300 relative to cable 910 may be configured to apply a force to a portion of housing tube 300. Illustratively, an application of a force to a portion of housing tube 300 may be configured to cause housing tube 300 to gradually curve, e.g., by compressing a portion of housing tube 300. For example, an application of a force to a portion of housing tube 300 may be configured to compress first housing tube portion 320 causing housing tube 300 to gradually curve. In one or more embodiments, a gradual curving of housing tube 300 may be configured to gradually curve optic fiber 310, e.g., from an optic fiber in a third curved position 1130 to an optic fiber in a fourth curved position 1140. In one or more embodiments, a line tangent to optic fiber distal end 311 may be parallel to a line tangent to housing tube proximal end 302, e.g., when optic fiber 310 comprises an optic fiber in a fourth curved position 1140.

In one or more embodiments, one or more properties of a steerable laser probe may be adjusted to attain one or more desired steerable laser probe features. Illustratively, a length that housing tube distal end 301 extends from actuation mechanism distal end 711 may be adjusted to vary an amount of actuation of an actuation control 720 of a plurality of actuation controls 720 configured to curve housing tube 300 to a particular curved position. In one or more embodiments, a stiffness of first housing tube portion 320 or a stiffness of second housing tube portion 330 may be adjusted to vary an amount of actuation of an actuation control 720 of a plurality of actuation controls 720 configured to curve housing tube 300 to a particular curved position. Illustratively, a material comprising first housing tube portion 320 or a material comprising second housing tube portion 330 may be adjusted to vary an amount of actuation of an actuation control 720 of a plurality of actuation controls 720 configured to curve housing tube 300 to a particular curved position.

In one or more embodiments, a number of apertures in housing tube 300 may be adjusted to vary an amount of actuation of an actuation control 720 of a plurality of actuation controls 720 configured to curve housing tube 300 to a particular curved position. Illustratively, a location of one or more apertures in housing tube 300 may be adjusted to vary an amount of actuation of an actuation control 720 of a plurality of actuation controls 720 configured to curve housing tube 300 to a particular curved position. In one or more embodiments, a geometry of one or more apertures in housing tube 300 may be adjusted to vary an amount of actuation of an actuation control 720 of a plurality of actuation controls 720 configured to curve housing tube 300 to a particular curved position. Illustratively, a geometry of one or more apertures in housing tube 300 may be uniform, e.g., each aperture of the one or more apertures may have a same geometry. In one or more embodiments, a geometry of one or more apertures in housing tube 300 may be non-uniform, e.g., a first aperture in housing tube 300 may have a first geometry and a second aperture in housing tube 300 may have a second geometry. Illustratively, a geometry or location of one or more apertures in housing tube 300 may be optimized to evenly distribute an applied force. For example, a geometry or location of one or more apertures in housing tube 300 may be optimized to evenly distribute a compressive force applied to first housing tube portion 320.

Illustratively, a stiffness of first housing tube portion 320 or a stiffness of second housing tube portion 330 may be adjusted to vary a bend radius of housing tube 300. In one or more embodiments, a stiffness of first housing tube portion 320 or a stiffness of second housing tube portion 330 may be adjusted to vary a radius of curvature of housing tube 300, e.g., when housing tube 300 is in a particular curved position. Illustratively, a number of apertures in housing tube 300 may be adjusted to vary a bend radius of housing tube 300. In one or more embodiments, a number of apertures in housing tube 300 may be adjusted to vary a radius of curvature of housing tube 300, e.g., when housing tube 300 is in a particular curved position. Illustratively, a location or a geometry of one or more apertures in housing tube 300 may be adjusted to vary a bend radius of housing tube 300. In one or more embodiments, a location or a geometry of one or more apertures in housing tube 300 may be adjusted to vary a radius of curvature of housing tube 300, e.g., when housing tube 300 is in a particular curved position.

In one or more embodiments, a geometry of actuation mechanism 710 may be adjusted to vary an amount of actuation of an actuation control 720 of a plurality of actuation controls 720 configured to curve housing tube 300 to a particular curved position. Illustratively, a geometry of actuation mechanism guide 780 may be adjusted to vary an amount of actuation of an actuation control 720 of a plurality of actuation controls 720 configured to curve housing tube 300 to a particular curved position. In one or more embodiments, a geometry of handle end cap 705 or a geometry of handle base 730 may be adjusted to vary an amount of actuation of an actuation control 720 of a plurality of actuation controls 720 configured to curve housing tube 300 to a particular curved position. Illustratively, one or more locations within housing tube 300 wherein optic fiber 310 may be fixed to a portion of housing tube 300 may be adjusted to vary an amount of actuation of an actuation control 720 of a plurality of actuation controls 720 configured to curve housing tube 300 to a particular curved position.

In one or more embodiments, at least a portion of optic fiber 310 may be enclosed in an optic fiber sleeve configured to, e.g., protect optic fiber 310, vary a stiffness of optic fiber 310, vary an optical property of optic fiber 310, etc. Illustratively, optic fiber 310 may comprise a buffer, a cladding disposed in the buffer, and a core disposed in the cladding. In one or more embodiments, at least a portion of optic fiber 310 may comprise a buffer configured to protect an optical property of optic fiber 310. Illustratively, at least a portion of optic fiber 310 may comprise a buffer configured to protect an optical layer of optic fiber 310, e.g., the buffer may protect an optical layer of a curved portion of optic fiber 310. In one or more embodiments, at least a portion of optic fiber 310 may comprise a polyimide buffer configured to protect an optical property of optic fiber 310. For example, at least a portion of optic fiber 310 may comprise a Kapton buffer configured to protect an optical property of optic fiber 310.

Illustratively, a steerable laser probe may be configured to indicate, e.g., to a surgeon, a direction that optic fiber 310 may curve, e.g., due to an actuation of an actuation control 720 of a plurality of actuation controls 720. In one or more embodiments, a portion of a steerable laser probe, e.g., handle 800, may be marked in a manner configured to indicate a direction that optic fiber 310 may curve. For example, a portion of housing tube 300 may comprise a mark configured to indicate a direction that optic fiber 310 may curve. Illustratively, housing tube 300 may comprise a slight curve, e.g., a curve less than 7.5 degrees, when an actuation control 720 of a plurality of actuation controls 720 is fully retracted relative to an actuation control guide proximal end 812. In one or more embodiments, housing tube 300 may comprise a slight curve configured to indicate a direction that optic fiber 310 may curve, e.g., due to an extension of an actuation control 720 of a plurality of actuation controls 720 relative to an actuation control guide proximal end 812.

In one or more embodiments, a steerable laser probe may comprise a pressure mechanism configured to provide a force. Illustratively, a pressure mechanism may be disposed within pressure mechanism housing 785. For example, a pressure mechanism may be disposed within proximal chamber 740. In one or more embodiments, a pressure mechanism may be configured to provide a constant force. Illustratively, a pressure mechanism may be configured to provide a variable force. In one or more embodiments, a pressure mechanism may be configured to provide a resistive force, e.g., to resist an extension of actuation mechanism 710 relative to handle proximal end 802. Illustratively, a pressure mechanism may be configured to provide a facilitating force, e.g., to facilitate a retraction of actuation mechanism 710 relative to handle proximal end 802. In one or more embodiments, a pressure mechanism may be configured to provide a resistive force, e.g., to resist a retraction of actuation mechanism 710 relative to handle proximal end 802. Illustratively, a pressure mechanism may be configured to provide a facilitating force, e.g., to facilitate an extension of actuation mechanism 710 relative to handle proximal end 802. In one or more embodiments, a pressure mechanism may comprise a spring or a coil. Illustratively, a pressure mechanism may comprise a pneumatic system or any system configured to provide a force.

In one or more embodiments, one or more actuation controls 720 may be fixed together. For example, a first actuation control 720 may be connected to a second actuation control 720 wherein an actuation of the first actuation control 720 is configured to actuate the second actuation control 720 and an actuation of the second actuation control 720 is configured to actuate the first actuation control 720. Illustratively, each actuation control 720 of a plurality of actuation controls 720 may be connected wherein an actuation of a particular actuation control 720 is configured to actuate each actuation control 720 of the plurality of actuation controls 720. In one or more embodiments, each actuation control 720 may be connected to another actuation control 720 of a plurality of actuation controls 720, e.g., by a ring or any suitable structure wherein a surgeon may actuate each actuation control 720 of the plurality of actuation controls 720 in any rotational orientation of handle 800.

Illustratively, handle 800 may comprise one or more detents configured to temporarily house an actuation control 720 of a plurality of actuation controls 720. In one or more embodiments, an actuation control guide 810 may comprise one or more detents configured to temporarily fix an actuation control 720 in a position relative to handle proximal end 802. Illustratively, a surgeon may actuate an actuation control 720 of a plurality of actuation controls 720 into a detent of an actuation control guide 810, e.g., to temporarily fix an actuation control 720 in a position relative to handle proximal end 802. In one or more embodiments, temporarily fixing an actuation control 720 of a plurality of actuation controls 720 in a position relative to handle proximal end 802 may be configured to temporarily fix housing tube 300 in a particular curved position. Illustratively, a surgeon may actuate an actuation control 720 out from a detent of an actuation control guide 810, e.g., to adjust an amount of actuation of an actuation control 720 relative to handle proximal end 802. In one or more embodiments, adjusting an amount of actuation of an actuation control 720 relative to handle proximal end 802 may be configured to adjust a curvature of housing tube 300.

Illustratively, cable 910 may be fixed to housing tube 300 at a plurality of fixation points, e.g., to vary one or more properties of a steerable laser probe. In one or more embodiments, a length of cable 910 may be adjusted to vary an amount of extension of an actuation control 720 of a plurality of actuation controls 720 relative to handle proximal end 802 configured to curve housing tube 300 to a particular curved position. Illustratively, a steerable laser probe may comprise one or more redundant cables 910. In one or more embodiments, one or more redundant cables 910 may be configured to maintain a particular curved position of housing tube 300, e.g., in the event that cable 910 breaks or fails. Illustratively, one or more redundant cables 910 may be configured to maintain a particular curved position of housing tube 300, e.g., in the event that a cable 910 fixation means fails. In one or more embodiments, one or more redundant cables 910 may be configured to maintain a particular curved position of housing tube 300, e.g., in the event that cable 910 is no longer configured to maintain the particular curved position of housing tube 300. Illustratively, one or more redundant cables 910 may be configured to maintain a particular curved position of housing tube 300 wherein cable 910 is also configured to maintain the particular curved position of housing tube 300.

In one or more embodiments, housing tube 300 may comprise an access window configured to allow access to a portion cable 910. Illustratively, cable 910 may be fixed to a portion of housing tube 300, e.g., by looping a portion of cable 910 through an aperture in housing tube 300. In one or more embodiments, cable 910 may be fixed to a portion of housing tube 300, e.g., by a purely mechanical means. For example, cable 910 may be fixed to a portion of housing tube 300 in a manner other than by an adhesive, a weld, etc. Illustratively, cable 910 may be fixed to a portion of housing tube 300 wherein a portion of cable 910 is configured to fail at a first applied failure force and a fixation means that fixes a portion of cable 910 to a portion of housing tube 300 is configured to fail at a second applied failure force. In one or more embodiments, the second applied failure force may be greater than the first applied failure force.

Figure 12A:
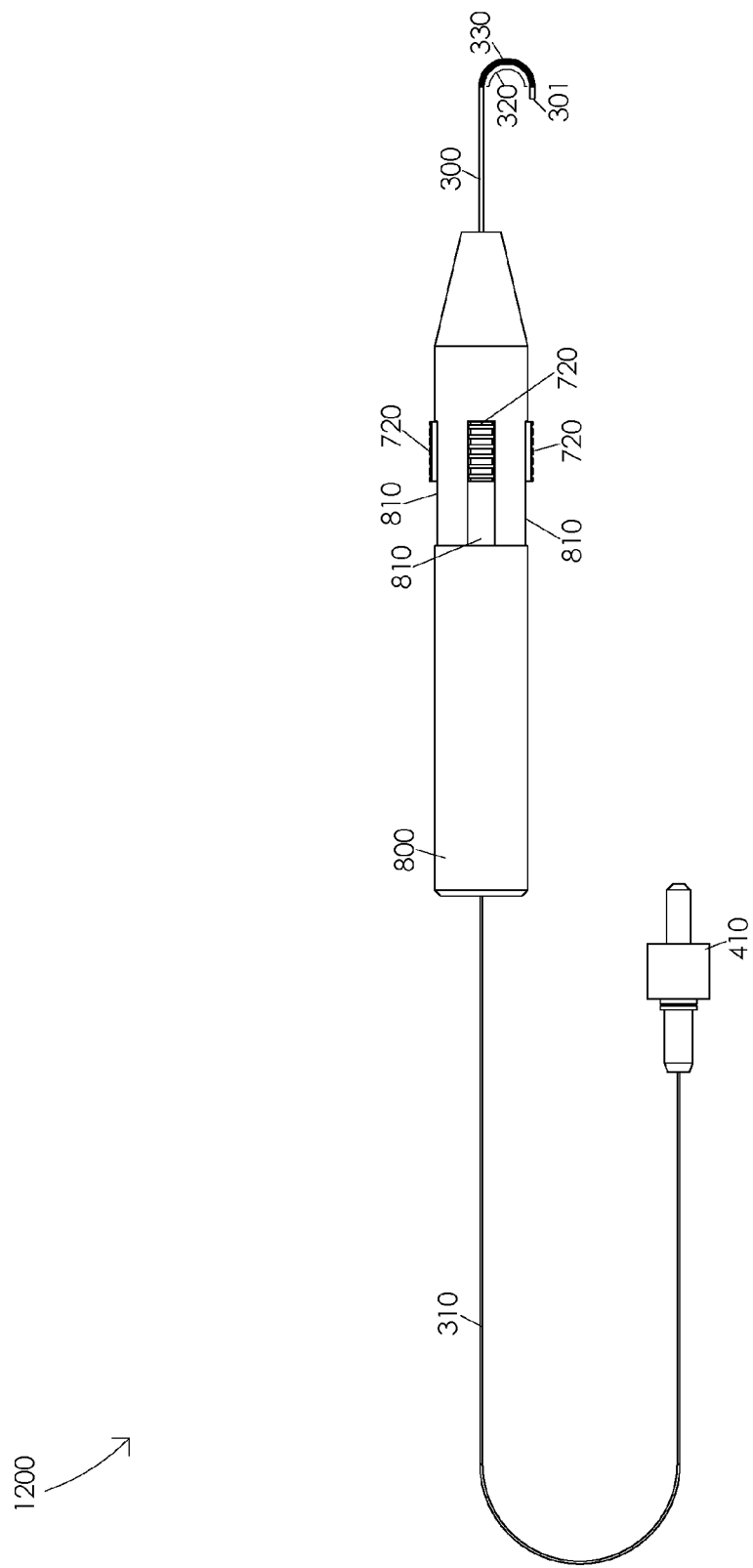
FIGS. 12A, 12B, 12C, 12D, and 12E are schematic diagrams illustrating a gradual straightening of an optic fiber.

FIGS. 12A, 12B, 12C, 12D, and 12E are schematic diagrams illustrating a gradual straightening of an optic fiber 310. FIG. 12A illustrates a fully curved optic fiber 1200. In one or more embodiments, optic fiber 310 may comprise a fully curved optic fiber 1200, e.g., when housing tube 300 is fully extended relative to handle proximal end 802. Illustratively, optic fiber 310 may comprise a fully curved optic fiber 1200, e.g., when an actuation control 720 of a plurality of actuation controls 720 is fully extended relative to an actuation control guide proximal end 812. In one or more embodiments, optic fiber 310 may comprise a fully curved optic fiber 1200, e.g., when actuation mechanism 710 is fully extended relative to handle proximal end 802. For example, optic fiber 310 may comprise a fully curved optic fiber 1200, e.g., when first housing tube portion 320 is fully compressed. Illustratively, a line tangent to optic fiber distal end 311 may be parallel to a line tangent to housing tube proximal end 302, e.g., when optic fiber 310 comprises a fully curved optic fiber 1200.

Figure 12B:
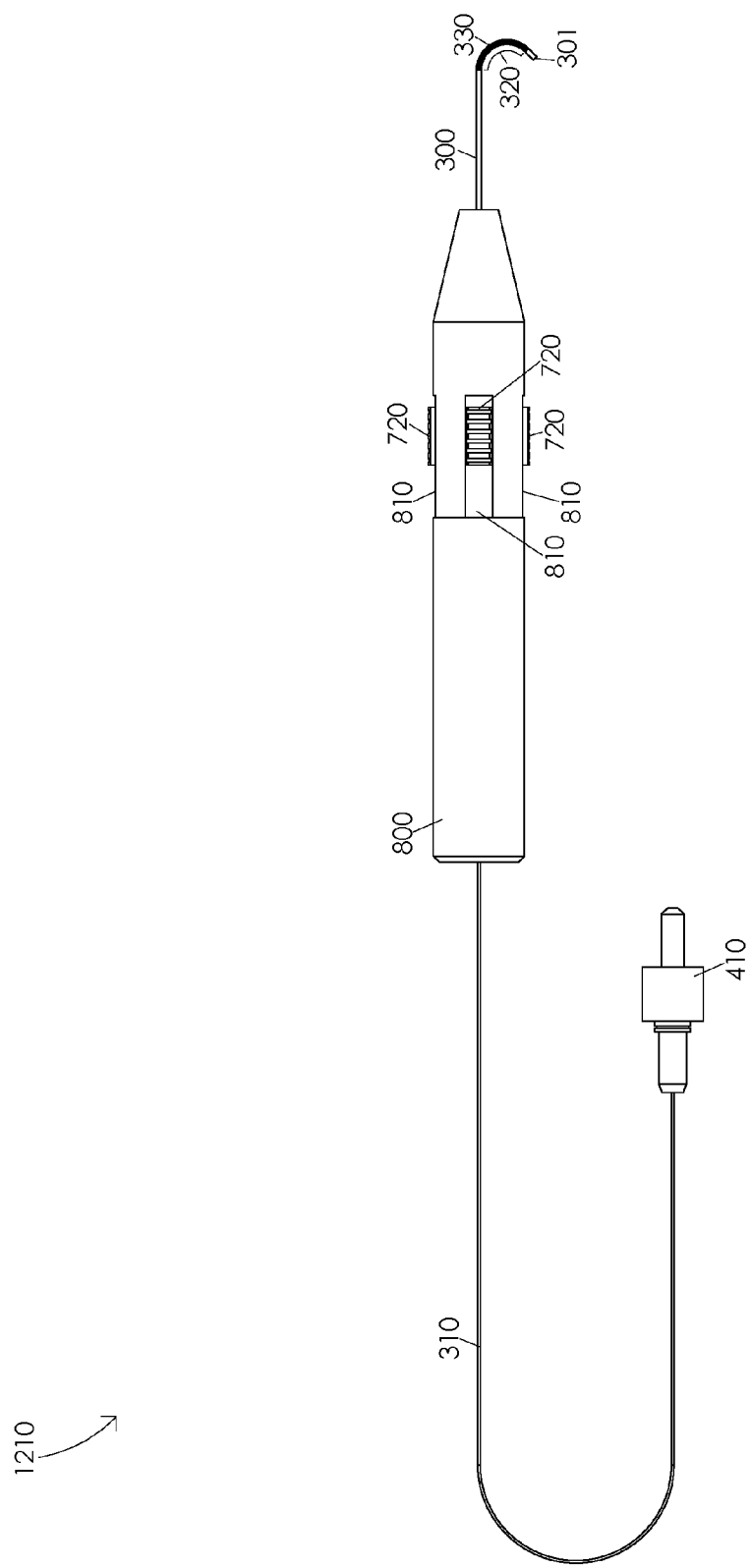

FIG. 12B illustrates an optic fiber in a first partially straightened position 1210. In one or more embodiments, an actuation of an actuation control 720 within an actuation control guide 810, e.g., towards actuation control guide proximal end 812 and away from actuation control guide distal end 811, may be configured to gradually straighten optic fiber 310 from a fully curved optic fiber 1200 to an optic fiber in a first partially straighten position 1210. Illustratively, an actuation of an actuation control 720 within an actuation control guide 810, e.g., towards actuation control guide proximal end 812 and away from actuation control guide distal end 811, may be configured to retract actuation mechanism 710 relative to cable 910. In one or more embodiments, a retraction of actuation mechanism 710 relative to cable 910 may be configured to retract housing tube 300 relative to cable 910. Illustratively, a portion of cable 910, e.g., a portion of cable 910 fixed to a portion of housing tube 300, may be configured to facilitate a retraction of housing tube 300 relative to cable 910. In one or more embodiments, a retraction of housing tube 300 relative to cable 910 may be configured to reduce a force applied to a portion of housing tube 300. Illustratively, a reduction of a force applied to a portion of housing tube 300 may be configured to cause housing tube 300 to gradually straighten, e.g., by decompressing a portion of housing tube 300. For example, a reduction of a force applied to a portion of housing tube 300 may be configured to decompress first housing tube portion 320 causing housing tube 300 to gradually straighten. In one or more embodiments, a gradual straightening of housing tube 300 may be configured to gradually straighten optic fiber 310, e.g., from a fully curved optic fiber 1200 to an optic fiber in a first partially straightened position 1210. In one or more embodiments, a line tangent to optic fiber distal end 311 may intersect a line tangent to housing tube proximal end 302 at a first partially straightened angle, e.g., when optic fiber 310 comprises an optic fiber in a first partially straightened position 1210. Illustratively, the first partially straightened angle may comprise any angle less than 180 degrees. For example, the first partially straightened angle may comprise a 135 degree angle.

Figure 12C:
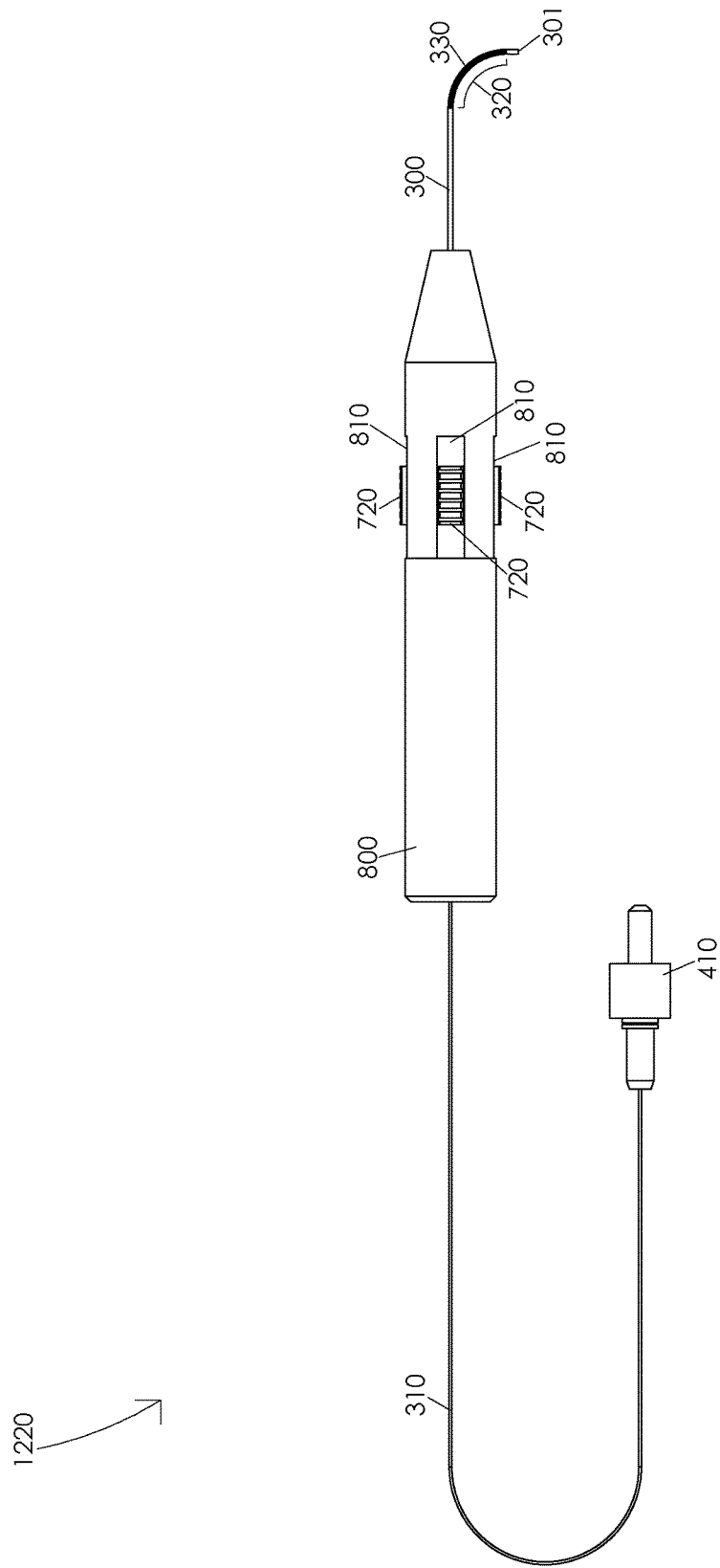

FIG. 12C illustrates an optic fiber in a second partially straightened position 1220. In one or more embodiments, an actuation of an actuation control 720 within an actuation control guide 810, e.g., towards actuation control guide proximal end 812 and away from actuation control guide distal end 811, may be configured to gradually straighten optic fiber 310 from an optic fiber in a first partially straighten position 1210 to an optic fiber in a second partially straightened position 1220. Illustratively, an actuation of an actuation control 720 within an actuation control guide 810, e.g., towards actuation control guide proximal end 812 and away from actuation control guide distal end 811, may be configured to retract actuation mechanism 710 relative to cable 910. In one or more embodiments, a refraction of actuation mechanism 710 relative to cable 910 may be configured to retract housing tube 300 relative to cable 910. Illustratively, a portion of cable 910, e.g., a portion of cable 910 fixed to a portion of housing tube 300, may be configured to facilitate a retraction of housing tube 300 relative to cable 910. In one or more embodiments, a retraction of housing tube 300 relative to cable 910 may be configured to reduce a force applied to a portion of housing tube 300. Illustratively, a reduction of a force applied to a portion of housing tube 300 may be configured to cause housing tube 300 to gradually straighten, e.g., by decompressing a portion of housing tube 300. For example, a reduction of a force applied to a portion of housing tube 300 may be configured to decompress first housing tube portion 320 causing housing tube 300 to gradually straighten. In one or more embodiments, a gradual straightening of housing tube 300 may be configured to gradually straighten optic fiber 310, e.g., from an optic fiber in a first partially straightened position 1210 to an optic fiber in a second partially straightened position 1220. In one or more embodiments, a line tangent to optic fiber distal end 311 may intersect a line tangent to housing tube proximal end 302 at a second partially straightened angle, e.g., when optic fiber 310 comprises an optic fiber in a second partially straightened position 1220. Illustratively, the second partially straightened angle may comprise any angle less than the first partially straightened angle. For example, the second partially straightened angle may comprise a 90 degree angle.

Figure 12D:
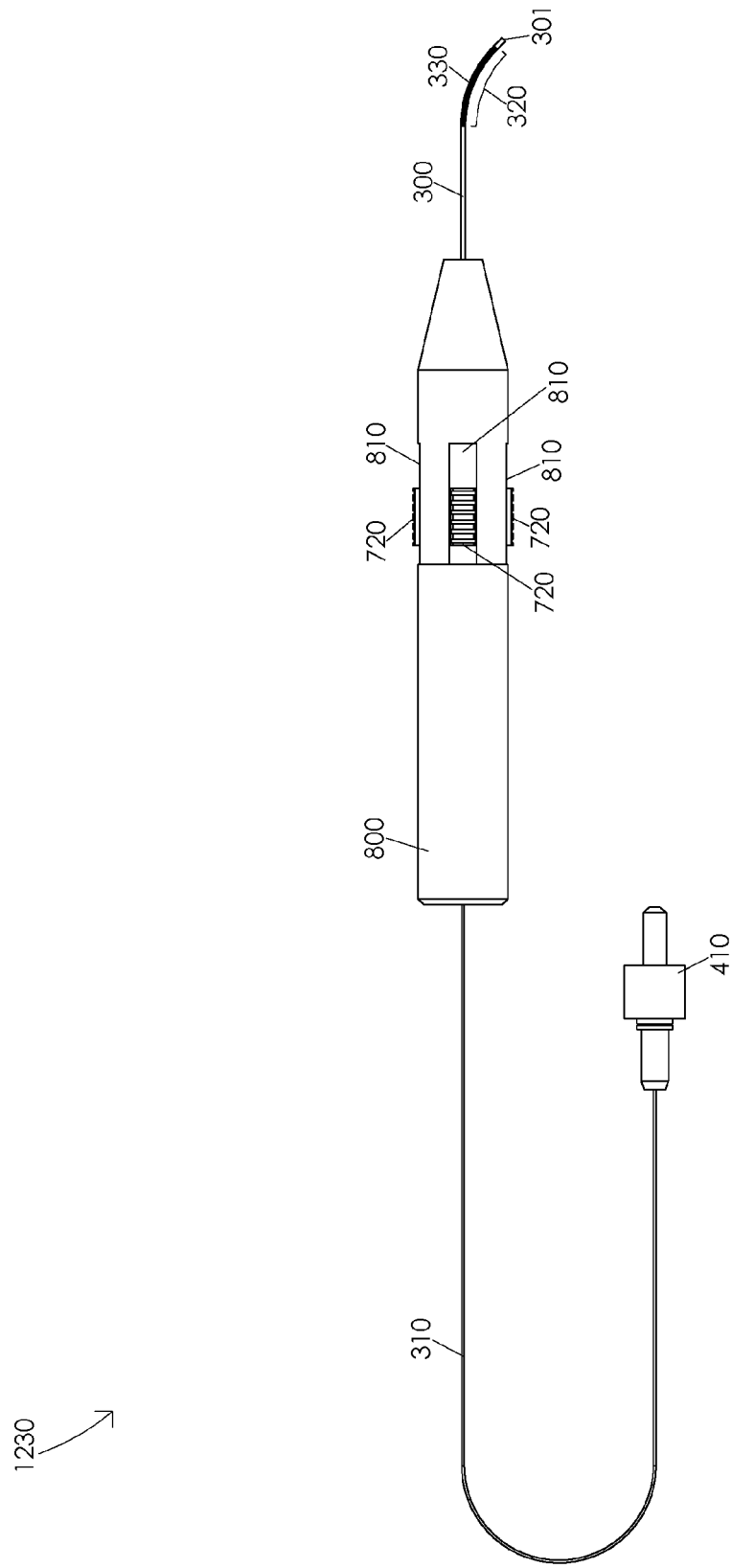

FIG. 12D illustrates an optic fiber in a third partially straightened position 1230. In one or more embodiments, an actuation of an actuation control 720 within an actuation control guide 810, e.g., towards actuation control guide proximal end 812 and away from actuation control guide distal end 811, may be configured to gradually straighten optic fiber 310 from an optic fiber in a second partially straightened position 1220 to an optic fiber in a third partially straightened position 1230. Illustratively, an actuation of an actuation control 720 within an actuation control guide 810, e.g., towards actuation control guide proximal end 812 and away from actuation control guide distal end 811, may be configured to retract actuation mechanism 710 relative to cable 910. In one or more embodiments, a retraction of actuation mechanism 710 relative to cable 910 may be configured to retract housing tube 300 relative to cable 910. Illustratively, a portion of cable 910, e.g., a portion of cable 910 fixed to a portion of housing tube 300, may be configured to facilitate a retraction of housing tube 300 relative to cable 910. In one or more embodiments, a refraction of housing tube 300 relative to cable 910 may be configured to reduce a force applied to a portion of housing tube 300. Illustratively, a reduction of a force applied to a portion of housing tube 300 may be configured to cause housing tube 300 to gradually straighten, e.g., by decompressing a portion of housing tube 300. For example, a reduction of a force applied to a portion of housing tube 300 may be configured to decompress first housing tube portion 320 causing housing tube 300 to gradually straighten. In one or more embodiments, a gradual straightening of housing tube 300 may be configured to gradually straighten optic fiber 310, e.g., from an optic fiber in a second partially straightened position 1220 to an optic fiber in a third partially straightened position 1230. In one or more embodiments, a line tangent to optic fiber distal end 311 may intersect a line tangent to housing tube proximal end 302 at a third partially straightened angle, e.g., when optic fiber 310 comprises an optic fiber in a third partially straightened position 1230. Illustratively, the third partially straightened angle may comprise any angle less than the second partially straightened angle. For example, the third partially straightened angle may comprise a 45 degree angle.

Figure 12E:
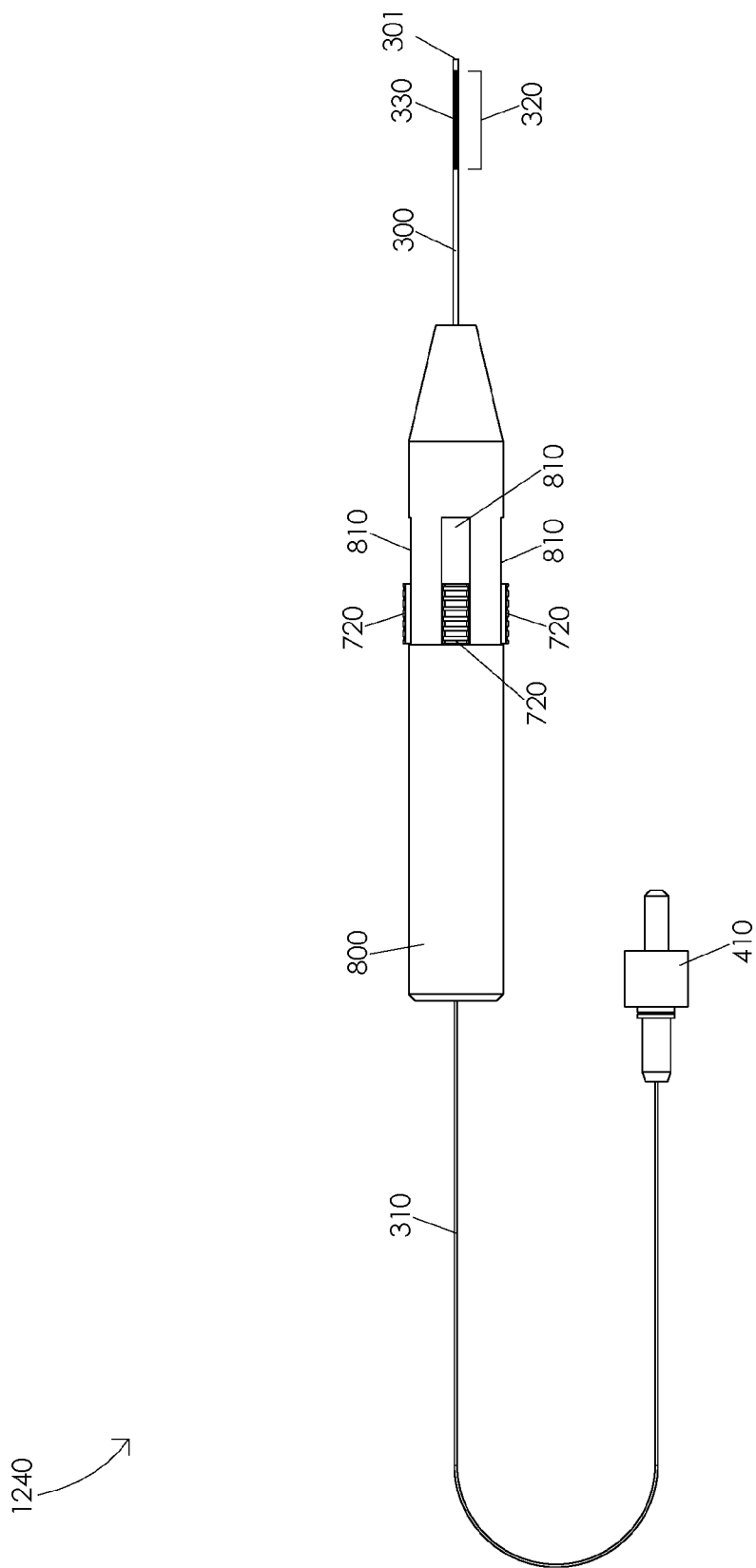

FIG. 12E illustrates an optic fiber in a fully straightened position 1240. In one or more embodiments, an actuation of an actuation control 720 within an actuation control guide 810, e.g., towards actuation control guide proximal end 812 and away from actuation control guide distal end 811, may be configured to gradually straighten optic fiber 310 from an optic fiber in a third partially straightened position 1230 to an optic fiber in a fully straightened position 1240. Illustratively, an actuation of an actuation control 720 within an actuation control guide 810, e.g., towards actuation control guide proximal end 812 and away from actuation control guide distal end 811, may be configured to retract actuation mechanism 710 relative to cable 910. In one or more embodiments, a retraction of actuation mechanism 710 relative to cable 910 may be configured to retract housing tube 300 relative to cable 910. Illustratively, a portion of cable 910, e.g., a portion of cable 910 fixed to a portion of housing tube 300, may be configured to facilitate a retraction of housing tube 300 relative to cable 910. In one or more embodiments, a retraction of housing tube 300 relative to cable 910 may be configured to reduce a force applied to a portion of housing tube 300. Illustratively, a reduction of a force applied to a portion of housing tube 300 may be configured to cause housing tube 300 to gradually straighten, e.g., by decompressing a portion of housing tube 300. For example, a reduction of a force applied to a portion of housing tube 300 may be configured to decompress first housing tube portion 320 causing housing tube 300 to gradually straighten. In one or more embodiments, a gradual straightening of housing tube 300 may be configured to gradually straighten optic fiber 310, e.g., from an optic fiber in a third partially straightened position 1230 to an optic fiber in a fully straightened position 1240. In one or more embodiments, a line tangent to optic fiber distal end 311 may be parallel to a line tangent to housing tube proximal end 302, e.g., when optic fiber 310 comprises an optic fiber in a fully straightened position 1240.

Illustratively, a surgeon may aim optic fiber distal end 311 at any of a plurality of targets within an eye, e.g., to perform a photocoagulation procedure, to illuminate a surgical target site, etc. In one or more embodiments, a surgeon may aim optic fiber distal end 311 at any target within a particular transverse plane of the inner eye by, e.g., rotating handle 800 to orient housing tube 300 in an orientation configured to cause a curvature of housing tube 300 within the particular transverse plane of the inner eye and varying an amount of actuation of an actuation control 720 of a plurality of actuation controls 720. Illustratively, a surgeon may aim optic fiber distal end 311 at any target within a particular sagittal plane of the inner eye by, e.g., rotating handle 800 to orient housing tube 300 in an orientation configured to cause a curvature of housing tube 300 within the particular sagittal plane of the inner eye and varying an amount of actuation of an actuation control 720 of a plurality of actuation controls 720. In one or more embodiments, a surgeon may aim optic fiber distal end 311 at any target within a particular frontal plane of the inner eye by, e.g., varying an amount of actuation of an actuation control 720 of a plurality of actuation controls 720 to orient a line tangent to optic fiber distal end 311 wherein the line tangent to optic fiber distal end 311 is within the particular frontal plane of the inner eye and rotating handle 800. Illustratively, a surgeon may aim optic fiber distal end 311 at any target located outside of the particular transverse plane, the particular sagittal plane, and the particular frontal plane of the inner eye, e.g., by varying a rotational orientation of handle 800 and varying an amount of actuation of an actuation control 720 of a plurality of actuation controls 720. In one or more embodiments, a surgeon may aim optic fiber distal end 311 at any target of a plurality of targets within an eye, e.g., without increasing a length of a portion of a steerable laser probe within the eye. Illustratively, a surgeon may aim optic fiber distal end 311 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. An ophthalmic laser probe comprising:
   a handle having a handle distal end and a handle proximal end;
   a handle base of the handle;
   a housing tube guide of the handle base;
   an actuation mechanism guide of the handle base;
   a plurality of handle base channels of the handle base wherein each handle base channel of the plurality of handle base channels is separated from at least one handle base channel of the plurality of handle base channels by a handle base limb;
   a handle end cap of the handle having a handle end cap distal end, a handle end cap proximal end, and a handle base housing, the handle base proximal end disposed in the handle base housing wherein the handle end cap distal end is configured to interface with the handle end cap interface;
   an actuation control guide of the handle;
   an actuation mechanism of the handle having an actuation mechanism distal end and an actuation mechanism proximal end, the actuation mechanism disposed in the handle base;
   a housing tube housing of the actuation mechanism;
   an inner bore of the actuation mechanism;
   an actuation control of the actuation mechanism wherein the actuation control is disposed in the actuation control guide;
   a single housing tube having a housing tube distal end and housing tube proximal end, the housing tube disposed within the housing tube housing of the actuation mechanism and a housing tube guide of the handle base wherein the housing tube is fixed within the housing tube housing;
   a first housing tube portion of the housing tube having a first stiffness;
   a plurality of apertures of the first housing tube portion;
   a second housing tube portion of the housing tube having a second stiffness; and
   an optic fiber having an optic fiber distal end and an optic fiber proximal end, the optic fiber disposed in the inner bore, the housing tube housing, and the housing tube wherein an actuation of the actuation control towards the handle distal end and away from the handle proximal end is configured to extend the housing tube relative to a portion of the optic fiber that is fixed to the housing tube and curve the housing tube and the optic fiber.

2. The ophthalmic laser probe of claim 1 wherein an actuation of the actuation control is configured to gradually straighten the optic fiber.

3. The ophthalmic laser probe of claim 2 wherein the actuation of the actuation control is configured to gradually straighten the housing tube.

4. The ophthalmic laser probe of claim 1 further comprising:
   a slight curve of the housing tube distal end, the slight curve configured to indicate an optic fiber curvature direction.

5. The ophthalmic laser probe of claim 1 further comprising:
   a cable having a cable distal end and a cable proximal end, the cable disposed in the handle and the housing tube.

6. The ophthalmic laser probe of claim 5 wherein an actuation of the actuation control is configured to gradually straighten the optic fiber.

7. The ophthalmic laser probe of claim 6 wherein the actuation of the actuation control is configured to gradually straighten the housing tube.

8. The ophthalmic laser probe of claim 5 further comprising:
   a redundant cable having a redundant cable distal end and a redundant cable proximal end, the redundant cable disposed within the handle and the housing tube.

9. The ophthalmic laser probe of claim 8 wherein an actuation of the actuation control is configured to gradually straighten the optic fiber.

10. The ophthalmic laser probe of claim 9 wherein the actuation of the actuation control is configured to gradually straighten the housing tube.

11. The ophthalmic laser probe of claim 1 wherein the actuation of the actuation control towards the handle distal end and away from the handle proximal end is configured to extend the actuation mechanism relative to the optic fiber proximal end.

12. The ophthalmic laser probe of claim 1 wherein an actuation of the actuation control towards the handle proximal end and away from the handle distal end is configured to retract the actuation mechanism relative to the optic fiber proximal end.

13. The ophthalmic laser probe of claim 1 wherein the actuation of the actuation control towards the handle distal end and away from the handle proximal end is configured to compress the first housing tube portion.

14. The ophthalmic laser probe of claim 1 wherein the actuation of the actuation control towards the handle distal end and away from the handle proximal end is configured to curve the optic fiber by less than 45 degrees.

15. The ophthalmic laser probe of claim 1 wherein the actuation of the actuation control towards the handle distal end and away from the handle proximal end is configured to curve the optic fiber by 45 degrees.

16. The ophthalmic laser probe of claim 1 wherein the actuation of the actuation control towards the handle distal end and away from the handle proximal end is configured to curve the optic fiber by more than 45 degrees.

17. The ophthalmic laser probe of claim 1 wherein the optic fiber is configured to transmit laser light.

18. The ophthalmic laser probe of claim 1 wherein the optic fiber is configured to transmit illumination light.

19. The ophthalmic laser probe of claim 1 wherein an actuation of the actuation control towards the handle proximal end and away from the handle distal end is configured to straighten the optic fiber.

20. The ophthalmic laser probe of claim 1 wherein an actuation of the actuation control towards the handle proximal end and away from the handle distal end is configured to decompress the first housing tube portion.

* * * * *